US008076061B2

(12) United States Patent
Ge

(10) Patent No.: US 8,076,061 B2
(45) Date of Patent: Dec. 13, 2011

(54) METHOD AND COMPOSITION FOR CANCER DIAGNOSIS AND TREATMENT

(75) Inventor: Hui Ge, Gaithersburg, MD (US)

(73) Assignee: Ascentgene, Inc., College Park, MD (US)

( * ) Notice: Subject to any disclaimer, the term of this patent is extended or adjusted under 35 U.S.C. 154(b) by 85 days.

(21) Appl. No.: 12/230,785

(22) Filed: Sep. 4, 2008

(65) Prior Publication Data

US 2009/0098554 A1    Apr. 16, 2009

Related U.S. Application Data

(60) Provisional application No. 60/970,686, filed on Sep. 7, 2007.

(51) Int. Cl.
*C12Q 1/00* (2006.01)
(52) U.S. Cl. .......................................................... 435/4
(58) Field of Classification Search .................. None
See application file for complete search history.

(56) References Cited

U.S. PATENT DOCUMENTS

| | | | |
|---|---|---|---|
| 4,946,778 | A | 8/1990 | Ladner et al. |
| 5,132,405 | A | 7/1992 | Huston |
| 5,244,805 | A | 9/1993 | Miller |
| 5,476,786 | A | 12/1995 | Huston |
| 5,723,750 | A | 3/1998 | Stubbs |
| 6,278,039 | B1 | 8/2001 | Johnson |
| 2005/0272061 | A1 | 12/2005 | Petroziello et al. |
| 2007/0161018 | A1 | 7/2007 | Inazawa et al. |

FOREIGN PATENT DOCUMENTS

| | | |
|---|---|---|
| WO | WO/92/02529 | 2/1992 |
| WO | WO/00/04989 | 2/2000 |
| WO | WO/00/05377 | 2/2000 |
| WO | WO 01/25437 | 4/2001 |
| WO | WO/01/75177 | 10/2001 |
| WO | WO/03/008578 | 1/2003 |

OTHER PUBLICATIONS

Kretzschmar et al (Cell, 1994, 78: 525-534).*
Ge et al (PNAS, 1994, 91: 12691-12695).*
Guardavaccaro et al (Cell Growth & Differentiation, 1995, 6: 159-169).*
Ge and Roeder, (1994), Purification, cloning and characterization of a human coactivator, PC4, that mediates transcriptional activation of class II genes. Cell 78, 513-523.
Kretzschmar, M. et al., (1994) A novel mediator of class II gene transcription with homology to viral immediate-early transcriptional regulators. Cell 78, 525-534.
Kishore A. H. et al., (2007) p53 regulates its own activator-transcriptional coactivator PC4: a new p53 responsive gene. Biochem. J. BJ20070390.
Banerjee, S. et al. (2004) General transcriptional coactivator PC4 activates p53 function. Mol. Cell Biol. 24, 2052-2062.
Ge, H. et al., (1994) Phosphorylation negatively regulates the function of coactivator PC4. Proc. Natl. Acad. Sci. USA 91, 12691-12695.
Kumar, P.B.R. et al., (2001) p300-mediated acetylation of human transcriptional coactivator PC4 is inhibited by phosphorylation. J. Biol. Chem. 276, 16804-16809.
Pilch, B. et al., (2001) Specific inhibition of serine- and arginine-rich splicing factors phosphorylation, spliceosome assembly, and splicing by the antitumor drug NB-506. Cancer Res. 61, 6876-6884.
Chen, A.Y. et al., (2005) Silatecan DB-67 is a novel DNA topoisomerase I-targeted radiation sensitizer. Mol. Cancer Thera. 4, 317-324.
Das, C. et al., (2006) Transcripional coactivator PC4, a chromatin-associated protein, induces chromatin condensation. Mol. Cell. Biol. 26 8303-8315.
Kleivi, K. et al., (2007) Gene expression profiles of primary colorectal carcinomas, liver metastases, and carcinomatoses. Mol. Cancer 6, 1-16.
Domain antibodies (dAbs) (for review, see Holt et al., 2003, Trends in Biotechnology 21:484-490) are also suitable for the methods of the present invention.
Harlow and Lane, 1988, Antibodies: A Laboratory Manual. Cold Spring Harbor Laboratory Press, Cold Spring Harbor, NY.
Morrison et al., 1984, Proc. Natl. Acad. Sci. USA, 81:6851-6855.
Neuberger et al., 1984, Nature, 312:604-608.
Takeda et al., 1985, Nature, 314:452-454.
Huston et al., 1988, Proc. Natl. Acad. Sci. USA, 85:5879-5883.
Bird, 1988, Science, 242:423-426.
Ward et al., 1989, Nature, 334:544-546.
Wolff et al., 1984, Biochem. et Biophys. Acta, 802:259.
Hunter et al., 1975, J. Biol. Chem. 250: 409-17.
Manche et al., 1992, Mol. Cell. Biol. 12:5239-48.
Minks et al., 1979, J. Biol. Chem. 254:10180-3.
Elbashir et al., 2001, Nature 411: 494-8.
Bass, 2001, Nature 411:428-9.
Elbashir et al., 2001, Genes Dev. 15:188-200.
Jaeger et al., 1989, Proc. Natl. Acad. Sci. USA 86:7706.
Turner et al.., 1988, Annu. Rev. Biophys. Biophys. Chem. 17:167.
Kehlenback et al., 1998, J. Cell Biol. 141:863-74.
Ge, H. (2000) UPA, a universal protein array system for quantitative detection of protein-protein, protein-DNA, protein-RNA and protein-ligand interactions. Nucleic Acids Res. 28, e3.
PCT/CN08/072274 EPO Search Report of Nov. 23, 2010.
PCT/CN08/072274 PCT Patentability Report of Dec. 11, 2008.
PCT/CN08/072274 PCT Search Report of Dec. 11, 2008.
Wang et al., Mol. Cell. vol. 1(5):1097-2765 Apr. 5, 1998. Bielawski et al., Pharmaceutical Society of Japan vol. 29(7): 1493-1497 Jul. 1, 2006.
Meng et al., Current Topics in Medicinal Chemistry, Bentham Science Publishers, Netherlands, vol. 3(3): 305-320 Jan. 1, 2003.
Codegoni et al., Annals of Oncology vol. 9(3): 313-319 Mar. 3, 1998.
Ginger et al., Nature vol. 330(6149): 670-672 Date: 1987.
Van Hoy et al., Cell vol. 72(4): 587-594 Feb. 23, 1993.
Ansari et al., PNAS vol. 102(7): 2346-2349 Feb. 15, 2005.

* cited by examiner

*Primary Examiner* — Sean Aeder
(74) *Attorney, Agent, or Firm* — Remenick PLLC

(57) ABSTRACT

Methods and compositions for inhibiting the onset of cancer, and cancer diagnosis and treatment are provided. The treatment method comprises inhibiting the level or function of transcriptional positive factor 4 (PC4). Also provided are methods of screening for cancer inhibition agents based on inhibition of PC4 expression or function.

10 Claims, 13 Drawing Sheets

FIG. 1A (SEQ ID NO: 1)

```
gcgaacgacc aagagggtgt tcgactgcta gagccgagcg aagcgATGCC TAAATCAAAG GAACTTGTTT CTTCAAGCTC
TTCTGGCAGT GATTCTGACA GTGAGGTTGA CAAAAAGTTA AAGAGGAAAA AGCAAGTTGC TCCAGAAAAA CCTGTAAAGA
AACAAAAGAC AGGTGAGACT TCGAGAGCCC TGTCATCTTC TAAACAGAGC AGCAGCAGCA GAGATGATAA CATGTTTCAG
ATTGGGAAAA TGAGGTACGT TAGTGTTCGC GATTTTAAAG GCAAAGTGCT AATTGATATT AGAGAATATT GGATGGATCC
TGAAGGTGAA ATGAAACCAG GAAGAAAAGG TATTTCTTTA AATCCAGAAC AATGGAGCCA GCTGAAGGAA CAGATTTCTG
ACATTGATGA TGCAGTAAGA AAACTGTAAa attcgagcca tataaataaa acctgtactg ttctagttgt tttaatctgt
cttttacat tggcttttgt tttctaaatg ttctccaagc tattgtatgt ttggattgca gaagaatttg taagatgaat
actttttttt aatgtgcatt attaaaaata ttgagtgaag ctaattgtca acttattaa ggattacttt gtctgcccac
cacctagtgt aaaataaaat caagtaatac aatcttaact gttgtggcct ttttttgatca taagagttgg tactgtttaa
ggccaaaagt aacagttttt atagatcttt tagtttcaac tcagctttta caataaaaag gatttgtatt gcattgagtt
tataaacttt tggtttgtga acttcatatt tgatctttc tcttccaatc aaatgtctag gcttgtttga cttccacccc
caatggtttt tcactctttt tatttacttc attttccttt aataacttaa tctcttcatg ttcagttttt acttcactct
ttattctttt ctttgattat ggtatgctta tttggaaagt cagtgaaact gtcaaaatgt tatctcaata agatacttat
atgagaacta caatcaccga atctactgta ttcaatatta gcagatctaa tttgataaac aacatggctt gtgtgaaaac
tgagcaggtg tttgtttacc catagtgttc tgtgtagtta ttgcttagtc tgcagaaaat aatgacttag atgagatgtc
tgacttgctt tcacttatta aacatgttca ccatgggatg atgtctgtaa catcagatat tgttcaacta gactaggatt
taataaaaat tgtgaaagct tactggccta acattttatt ttataatatt gggtatgaat tatatgtagc cagagatgtc
attaagcttt actgttatag taggtaatat ggttagtttg tagggaaaag agcatatgag cacatgcttg tgtattttgg
cctttgcccc agtagaacag accaatggca ttctagactt gatgatacta agttttagca gacactagta agtggtttgt
atttaaccat actgatgaag cagacagatt gaggcacaga ttttagtggc tttgtggcaa taaatagggc atggtgtgcc
ttaggaaaag aatgtttata aagggaatta taactgaaat taaggaggc ggcagtgaag aggaaataat tctcttctat
ctaaatgata tacatatgat attttgagat ttttataaca gcagtggaac acaattctag gtagagtaga aaaaggaaag
tttaaagac atataaaaga ttccttgttga caaattattt ttggtagcaa atctcaaatg gttacctgct attaaggtct
gccatattag agttttgcac tatttgcta ccaagtttga ttcatacatc taaaacattt tgtagttact tgtcaaggac
ttaatttgaa aatcatttgc caggccacat agttatcaat ttttttttct atcagctatt ctgttgtatt tctaaaacat
tttttagatg acttttttaaa gtatatttag cagtaacctt atgaggttca aattggtaaa tctcttgtaa tttagccttc
atcgaataat aggtaccagt gtattaaaaa tgtgtatttt ttgcagcccc ttgaaccaga gtaggttcag agaaactccc
aagtttgta ctttagacac atcaagcttg attggtaact tccctccttt tttggggaac atgtttgtgt cctattaact
taattggata gattttttaaa tatttcttat ttttggcaca cggaaagggt agttcgagta cagaactttg atttttggtg
tagatgcaga gggaatgatg ggtaaatttc ctaggtttat gtgaatttag gggtgtatg cattttgaaa caatctacta
acagatggtg ctgaaatcta ttacctacat gttttctagt tgttcagcat tatgttaatg aagcctccat ataaggagtg
tttctctggc acagttggta agttgactgc taacttcatt taaatgtgtt actggatatg cagtatactg aaattattaa
tcagtttgtg tataggaaaa gagaactggg ttaaaagcaa attaacttgt tctgaaaaga aagtatagat taattttgtt
ttctgtttaa attttatctc cttggtaaag atttttttc ctgggcagaa aacttggcat tttaggcgt agataccta
ccttacaatg ccaaaatgaa tttaattcca gtactcaggt ttttcccttt aacagactct atgtgtatca gggcttcta
atgggttttt cctcttcgtt tttaaaatgt gagtagcatt tgaccaattt ccagtgctct tagcatttta cttaaagaac
aaccactaca aaagaaaatc tttgtaattt gattgtcttt tgctttgctt cattaatgcc taagaactta agaatactcc
tacctcatta gctactcaag atgctgtgac gatcaaatct attctacata atgcgtttag aaacaaagac ttgggtgaaa
aatgaaataa gtatattctg acttggctat tgaggggaaa attcagtatt aagtgttcct cacaggagat atgttagcag
aatactataa aagtttgaaa tttttaaaaa gtaaaagtac ttaaatttag gtatctctcc tgaaattctt tgcagttcat
tttttatggc agttaatcca gtgaaacact caaaagtttt tttttttttt aaaagtgttt ttccagataa actgtagggt
gaacattcac ataatcacaa atatgtaatt ctgtaattgt ggaatgcttg tatgctttgt tttcgtacat cttccatgga
gatgtctgaa tataatactc catctgtgaa tattttaaat gttgaaataa agtaagaaa tgtgaaaaaa aaaaaaaa
```

FIG 1B (SEQ ID NO: 3)

```
atgcctaaat caaaggaact tgtttcttca agctcttctg gcagtgattc
Tgacagtgag gttgacaaaa agttaaagag gaaaaagcaa gttgctccag
aaaaacctgt aaagaaacaa aagacaggtg agacttcgag agccctgtca
tcttctaaac agagcagcag cagcagagat gataacatgt ttcagattgg
gaaaatgagg tacgttagtg ttcgcgattt taaaggcaaa gtgctaattg
atattagaga atattggatg gatcctgaag gtgaaatgaa accaggaaga
aaaggtattt ctttaaatcc agaacaatgg agccagctga aggaacagat
ttctgacatt gatgatgcag taagaaaact gtaa
```

FIG. 1C (SEQ ID: 2)

```
MPKSKELVSS  GSSGSDSDSE  VDKKLKRKKQ  VAPEKPVKKQ  KTGETSRALS
SSKQSSSSRD  DNMFQIGKMR  YVSVRDFKGK  VLIDIREYWM  DPEGEMKPGR
KGISLNPEQW  SQLKEQISDI  DDAVRKL
```

FIG. 2

```
                                  20                    40
                               ** ** * * *
PC4-wt                    MPKSKELVSSSSSGSDSDSEVDKKLKRKKQVAPEKPVKKQKTGETSRALSSSKQSSSSRDDNMF
(SEQ ID NO: 2)

mt1                       ------------------------I-----A-------------------------------
(K23I/K29A)
(SEQ ID NO: 4)
mt2                       ----------------------------------I-----A---------------------
(K35I/K41A)
(SEQ ID NO: 5)
mt3                       ------------------------AIA-----------------------------------
(R27A/K28I/K29A)
(SEQ ID NO: 6)
mt4                       --------------------------------------------N-----I-----A-----
(R47N/K53I/R59A)
(SEQ ID NO: 7)
mt6                       ------------------------A-------------------------------------
(K29A)
(SEQ ID NO: 8)
mt7                       ----------------------------------------A---------------------
(K41A)
(SEQ ID NO: 9)
mt5                       QIGKMRYVSVRDFKGKVLIDIREYWMDPEGEMKPGRKGISLNPEQWSQLKEQISDIDDAVRKL
(F77P)                    ------------P-------------------------------------------------
(SEQ ID NO: 10)           65                  85                  105
```

FIG. 3
A. Purified Recombinant PC4 Protein
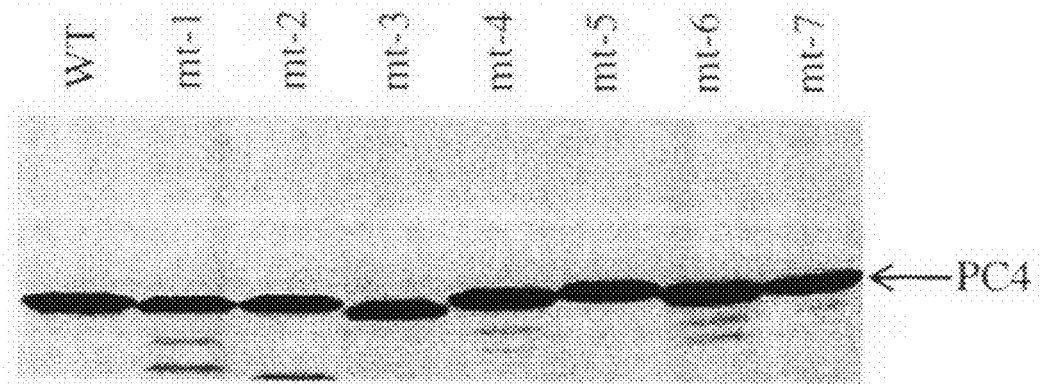
B. dsDNA-Binding Activity of PC4 (EMSA)
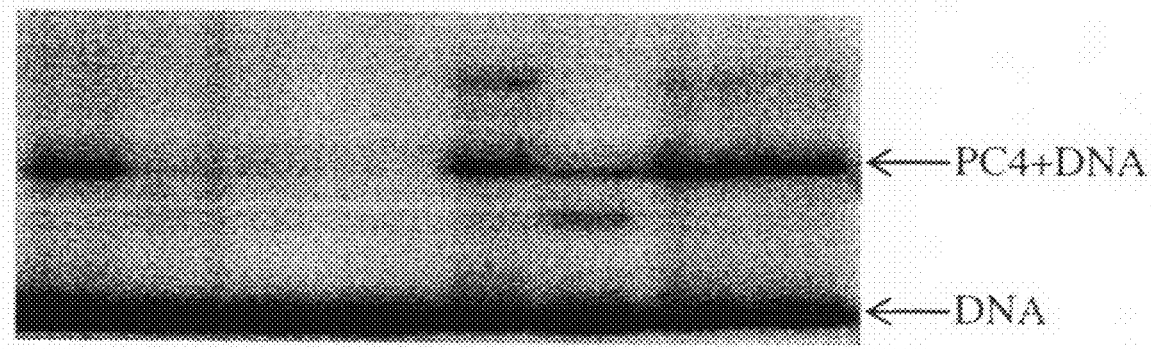
C. Transcription Activity of PC4
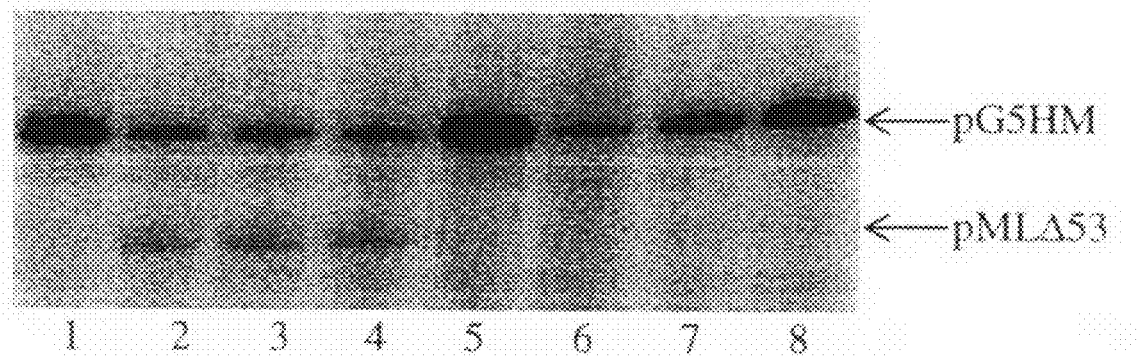

FIG. 7
A. Stained Gel
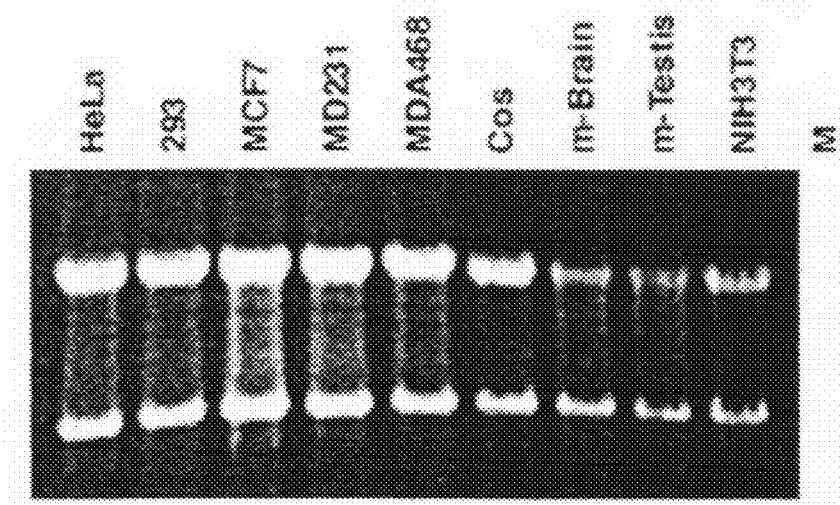
B. h-p52 probe
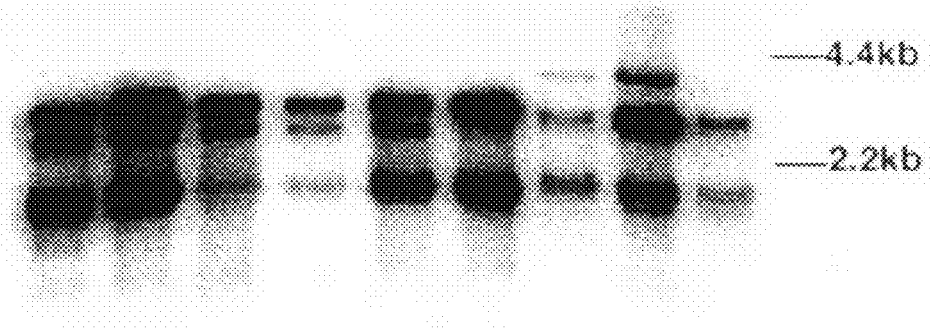
C. h-PC4 probe
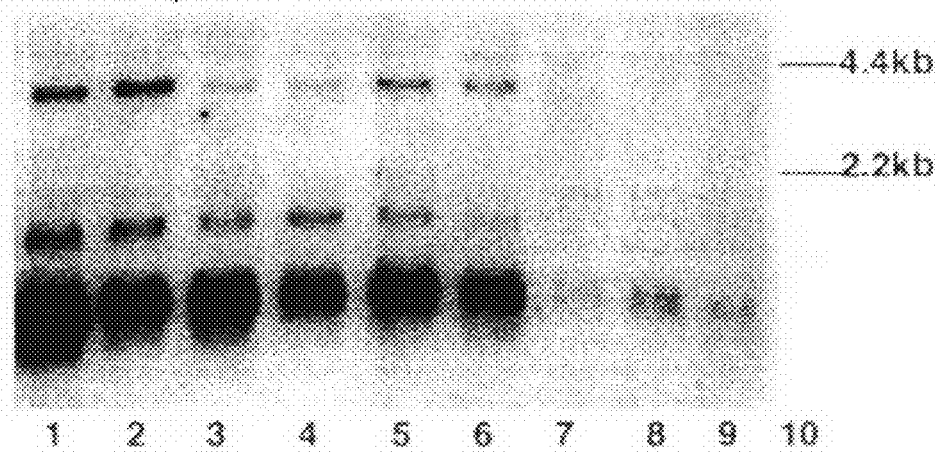

FIG. 9
A. Normal Lung Tissue
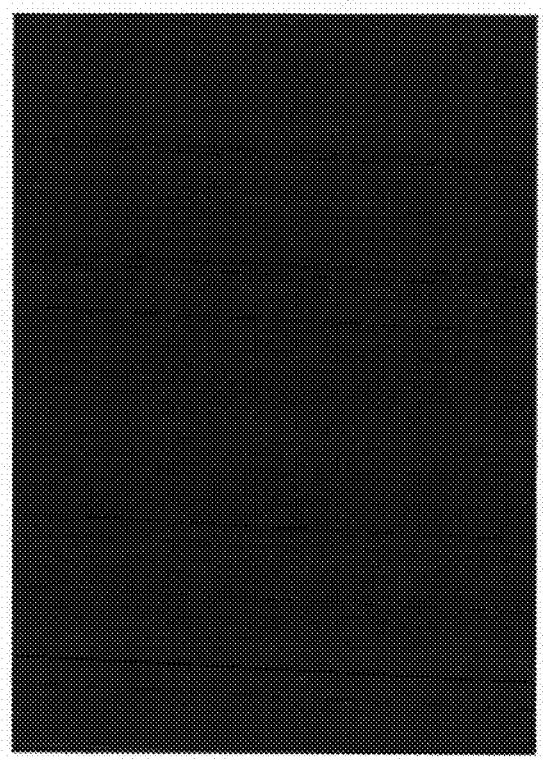
B. Lung Carcinoma
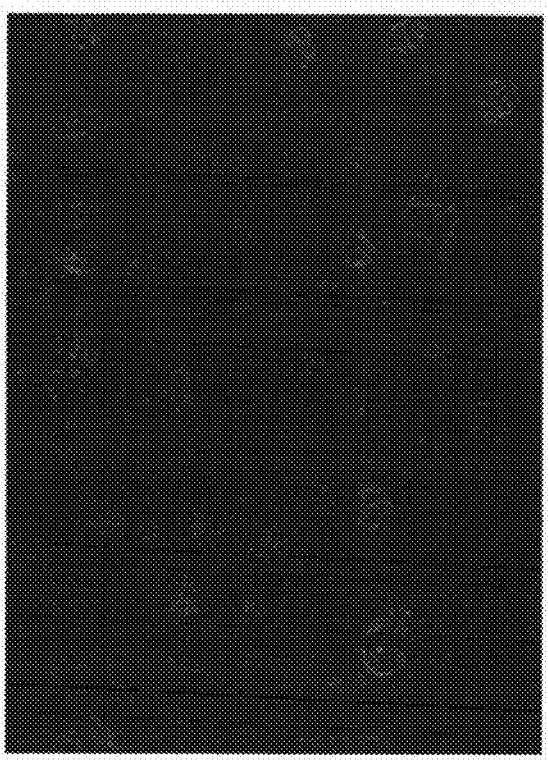

FIG. 11

1. KRKKQVAPEKPVKKQ (PC4-AD15) (SEQ ID NO: 11)

2. <u>PLSSIFSRIGDP</u>KRKKQVAPEKPVKKQ (TLD-AD15) (SEQ ID NO: 12)

3. DSDSEVDKKLKRKKQ (PC4-S15) (SEQ ID NO: 13)

4. <u>PLSSIFSRIGDP</u>DSDSEVDKKLKRKKQ (TLD-S15) (SEQ ID NO: 14)

5. ELQELQELQALLQQQ (AH15) (SEQ ID NO: 15)

6. <u>PLSSIFSRIGDP</u>ELQELQELQALLQQQ (TLD-AH15) (SEQ ID NO: 16)

7. <u>PLSSIFSRIGDP</u> (TLD12) (SEQ ID NO: 17)

METHOD AND COMPOSITION FOR CANCER DIAGNOSIS AND TREATMENT

CLAIM OF PRIORITY

This application claims the benefit of U.S. provisional patent application No. 60/970,686, filed Sep. 7, 2007.

FIELD OF THE INVENTION

This invention relates to methods and compositions for inhibition of cancer onset, cancer diagnosis and treatment. Specifically, the present invention relates to the expression and regulation of transcriptional positive cofactor 4 (PC4) in malignant tissue.

BACKGROUND OF THE INVENTION

The human transcriptional positive cofactor 4 (PC4, also known as p14, p15, Sub1 homolog, etc.) is a single-stranded DNA-binding protein of 127-amino acid residues with serine-rich regions near the N-terminus. This cofactor has been cloned and identified as a general positive cofactor that could mediate transcriptional activation of many genes by directly interacting with many sequence- and cell-specific regulators [Ge and Roeder, (1994), Purification, cloning and characterization of a human coactivator, PC4, that mediates transcriptional activation of class II genes. Cell 78, 513-523; Kretzschmar, M. et al., (1994) A novel mediator of class II gene transcription with homology to viral immediate-early transcriptional regulators. Cell 78, 525-534]. The regulators mediated by PC4 include many nuclear hormone receptors, tumor suppressors, onco-proteins and other important factors that are essential for tumorigenesis and pathogenesis of other human diseases.

The expression of PC4 is controlled by the tumor suppressor protein p53, which interacts with the PC4 protein itself at the transcription level. In addition, PC4 functions as a unique activator of p53 to regulate transcription of a number of genes involved in cell cycle, apoptosis, DNA repair and other cellular responses [Kishore A. H. et al., (2007) p53 regulates its own activator-transcriptional coactivator PC4: a new p53 responsive gene. Biochem. J. BJ20070390; Banerjee, S. et al. (2004) General transcriptional coactivator PC4 activates p53 function. Mol. Cell Biol. 24, 2052-2062]. PC4 activities can be further regulated by posttranslational modification at least including phosphorylation and acetylation. Phosphorylation of PC4 inhibits its activity to interact with targeted activators and negatively regulates its co-activator function. Mass spectrometric analyses suggest that the in vivo hyperphosphorylation of PC4 is mainly mediated by casein kinase II and restricted to the N-terminal serine-rich region [Ge, H. et al., (1994) Phosphorylation negatively regulates the function of coactivator PC4. Proc. Natl. Acad. Sci. USA 91, 12691-12695]. Acetylation of PC4 is mediated by p300 and inhibited by phosphorylation [Kumor, P. B. R. et al., (2001) p300-mediated acetylation of human transcriptional coactivator PC4 is inhibited by phosphorylation. J. Biol. Chem. 276, 16804-16809].

The roles of PC4 in regulatory genes related to cancer or tumorigenesis have been heretofore unclear. There is a need for improved molecular diagnosis of malignancy. In addition, there is a need for improved methods of screening for cancer inhibition agents as well as safe and effective cancer inhibition agents with enhanced tumor specificity and reduced toxicity to normal cells and tissues.

SUMMARY OF THE INVENTION

Accordingly, one object of the present invention is to provide a method for diagnosing a tumor in a subject by collecting a suitable sample from the subject and determining the level of PC4 protein. In one embodiment of the invention, identification of elevated PC4 level in a test sample as compared to a control sample indicates that the test sample is tumorous. In another embodiment elevated PC4 level in a test sample indicates a malignant tumor. In another embodiment of the invention, the method for diagnosing a tumor in a subject comprises additionally determining the level of DNA topoisomerase I in the test sample and comparing the level to a level of DNA topoisomerase I in a control sample. Accordingly, elevated DNA topoisomerase level in the test sample as compared to the control sample indicates that the test sample is tumorous.

Another object of the invention is to provide a method for diagnosing a tumor in a subject comprising determining a level of DNA topoisomerase I in the test sample and comparing the level to a level of DNA topoisomerase I in a control sample. Accordingly, elevated DNA topoisomerase level in the test sample as compared to the control sample indicates that the test sample is tumorous.

A further object of this invention is to provide a method for treating cancer or inhibiting the onset of cancer in a subject by decreasing the cellular level of PC4 or inhibiting the function of PC4 in the subject. In one embodiment of the invention, a pharmaceutical composition comprising an effective amount of an antagonist against PC4 protein is administered to the subject. In certain embodiments, the antagonist against PC4 protein is an anti-PC4 antibody, an antisense nucleic acid molecule based on PC4 coding sequence, a siRNA molecule based on PC4 gene sequence, or a modified non-functional PC4 peptide. In one embodiment, the modified non-functional PC4 peptide comprises a F77P point mutation. In another embodiment, the modified non-functional PC4 peptide comprises a phosphorylated PC4 protein or a suitable fragment or analog thereof.

A further object of the invention is to provide a method of screening for a cancer inhibition agent. In one embodiment of the invention the method is achieved by (1) providing a genetic construct comprising a promoter sequence of a PC4 gene operatively linked to a suitable reporter gene, and (2) contacting a candidate compound with the genetic construct under conditions suitable for the expression of the report gene, such that a candidate compound that inhibits the expression of the reporter gene is a cancer inhibition agent. In another embodiment of the invention, the method is achieved by (1) providing a PC4-dependent transcription assay, and (2) adding a candidate compound to the assay, such that a candidate compound that decreases PC4 transcription is a cancer inhibition agent. In yet another embodiment of the invention, the method is achieved by (1) providing a PC4-protein interaction assay, or a PC4-DNA interaction assay, and (2) adding a candidate compound to the assay, such that a candidate compound that decreases PC4-protein or PC4-DNA interaction is cancer inhibition agent.

A further object of the invention is to provide a method of monitoring cancer therapy in a subject. In one embodiment of the invention the method is achieved by collecting samples at various times during the course of therapy, determining the level of transcriptional positive cofactor 4 (PC4) protein in the samples, and comparing the level of transcriptional positive cofactor 4 (PC4) protein in the samples during the course of therapy, such that reduction in the level of transcriptional positive cofactor 4 (PC4) protein in a sample indicates successful cancer therapy. In other embodiments of the invention, the samples are simultaneously or independently examined for the expression of DNA topoisomerase I protein, such that reduction in such levels with increasing time of therapy is evidence of successful cancer therapy.

A further object of the invention is to provide use of mutated PC4 protein as a therapeutic drug to treat PC4-dependent tumors.

A further object of the invention is to provide use of short peptides corresponding to the activation domain of PC4 as cancer inhibition agents.

A further object of the invention is to provide use of an artificial activation domain as a cancer inhibition agent.

A further object of the invention is to provide use of a translocation domain (TLD) to facilitate entry of PC4 protein-related reagents to tumor cells.

A further object of the invention is to provide a high throughput system (HTS) for screening compounds that inhibit PC4 activity.

A further object of the invention, is to provide a method of treating cancer or inhibiting the onset of cancer further comprising administering to a subject one or more cancer inhibition agents.

These and other objects are achieved in the present invention.

The present invention overcomes a major limitation in the fields of inhibition of onset of cancer, cancer diagnosis and cancer treatment by providing methods for measuring the expression of the transcriptional cofactor PC4 and also methods for decreasing the expression of or function of PC4.

There has thus been outlined, rather broadly, the more important features of the invention in order that the detailed description thereof that follows may be better understood, and in order that the present contribution to the art may be better appreciated. There are, of course, additional features of the invention that will be described further hereinafter. Indeed, it is to be understood that both the foregoing general description and the following detailed description are exemplary and explanatory and are intended to provide further explanation of the invention as claimed.

In this respect, before explaining at least one embodiment of the invention in detail, it is to be understood that the invention is not limited in its application to the details of construction and to the arrangements of the components set forth in the following description, figures, or drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that equivalent constructions, insofar as they do not depart from the spirit and scope of the present invention, are included in the present invention.

The accompanying drawings are included to provide a further understanding of the invention and are incorporated in and constitute a part of this specification, illustrate several embodiments of the invention and together with the description serve to explain the principles of the invention.

BRIEF DESCRIPTION OF THE DRAWINGS

FIGS. 1A, 1B and 1C provide sequence information of human PC4. FIG. 1A shows the cDNA sequence and promoter region of human PC4 (GenBank Accession No. NM_006713). FIG. 1B shows the coding region of human PC4. FIG. 1C shows the amino acid sequence of human PC4. A point mutation at amino acid position 77 (F: phenylalanine; underlined) abolishes PC4 ssDNA binding activity.

FIG. 2 represents mutation analyses at the N-terminal region of PC4, including the basic region and F77.

FIGS. 3A, 3B and 3C show the functional analyses of PC4 mutations in different assays. FIG. 3A shows the normalization of various purified recombinant PC4 proteins (wild type; WT and mutation; mt). FIG. 3B shows the results of electrophoresis mobility shift assay (EMSA) for dsDNA binding activity of PC4. FIG. 3C shows the results of an in vitro transcription assay with PC4, where pG5HM is the template for PC4-dependent transcription and pMLΔ53 is the PC4-independent template.

FIG. 4C shows the interaction of PC4 and mutations with the transcription factor TFIIA. FIG. 4E shows the interaction of PC4 and mutation with the transcription factor Sp1. FIG. 4F shows the interaction of PC4 and mutations with ssDNA. FIGS. 4A and 4B confirm equal loading of samples and FIG. 4D is a control for non-specific binding to Gal4.

FIGS. 5A and 5B represent separate experiments examining stages 2 to 58 and 56 to 64, respectively, where "O" represents oocytes, "E" represents embryos, and PC4-P represents phosphorylated (inactive) form of PC4. FIG. 5C shows the correlation of PC4 activation with differentiation of *Xenopus laevis*. Data are shown for the effects of thyroid hormones T3 and T4, thyroid hormone receptors TRα and TRβ, and PC4.

FIG. 6A is the control (non-tranfected cells). FIG. 6B represents cells transfected with wild-type PC4. FIG. 6C represents cells transfected with serine-rich region mutations of PC4.

FIGS. 7A, 7B and 7C show that PC4 mRNA is detectable in transformed cell lines and breast cancer cell lines, but not in primary NIH3T3 cell line and non-malignant mouse tissues. FIG. 7A represents the quantification and equal loading of RNA samples. FIG. 7B shows the expression of p52 mRNA, another transcriptional co-activator in the various cell lines. FIG. 7C shows the expression of PC4 mRNA in the various cell lines.

FIG. 8B shows that PC4 protein is detectable in a number of human tumor tissues (T), but not in corresponding normal (N) human tissues. FIG. 8A indicates that the activation of PC4 correlates with the activation of DNA topoisomerase I, a well-studied target for several cancer inhibition drugs.

FIGS. 9A and 9B represents immunohistochemical (IHC) analysis of PC4 in human lung carcinoma. FIG. 9A shows that PC4 protein is not detectable in normal human lung tissue. FIG. 9B shows that PC4 protein accumulates in all tumor cells of human lung carcinoma tissue.

FIG. 11 provides the amino acid sequences of designed peptides for potential use as cancer inhibition agents.

DETAILED DESCRIPTION OF THE INVENTION

Figure 4:
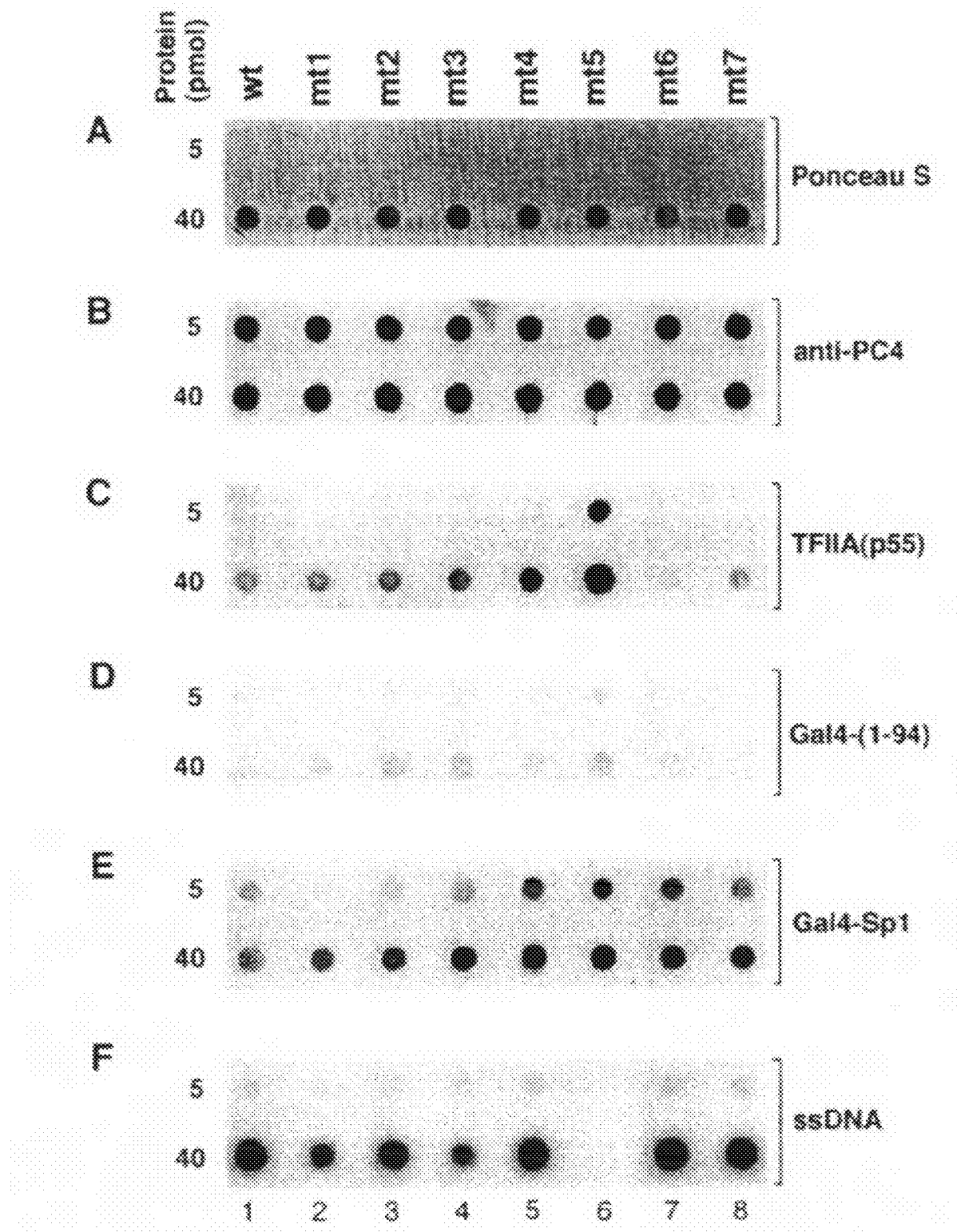
FIGS. 4A, 4B, 4C, 4D, 4E, and 4F illustrate the results of protein array analyses of various PC4 mutations.

Reference will now be made in detail to the embodiments of the invention, examples of which are illustrated in the accompanying drawings.

Using different systems including *Xenopus* oocytes, mammalian cell lines and human tissues, the present inventor surprisingly discovered that PC4 functions as an onco-protein and plays important roles in cell differentiation, development and pathogenesis of tumors. Specifically, PC4 was found to be activated at the protein level in a number of tumor tissues including lung cancer, bladder cancer, colon cancer, breast cancer, endometrial cancer, thyroid cancer, and small bowel cancer. In contrast, PC4 protein level in corresponding normal tissues that are not actively undergoing rapid development is not activated. The activation of PC4 at the mRNA level has been found in tumor cell lines and other transformed cell lines, but not in primary cell lines.

The activation of PC4 in tumor tissues is further correlated with the activation of DNA Topoisomerase I, an enzyme that relaxes DNA and is the target for several anti-cancer drugs such as NB-506, J-109,382, DB-67 [Pilch, B. et al., (2001) Specific inhibition of serine- and arginine-rich splicing factors phosphorylation, spliceosome assembly, and splicing by the antitumor drug NB-506. Cancer Res. 61, 6876-6884; Chen, A. Y. et al., (2005) Silatecan DB-67 is a novel DNA topoisomerase I-targeted radiation sensitizer. Mol. Cancer Thera. 4, 317-324].

Proteins encoded by many oncogenes and tumor suppressor genes, such as c-myc, p53, as well as DNA topoisomerase I are also known to function as transcription regulatory factors and their activities can be potentiated by the PC4.

The above data are consistent with the conclusion that, in addition to functioning as a transcription coactivator, PC4 also functions as an onco-protein to stimulate cell development, differentiation, malignant transformation and cancer progression. In fact, activations of PC4 during pathogenesis of cancers have been found at the RNA level from other studies using DNA array method [Das, C. et al., (2006) Transcripional coactivator PC4, a chromatin-associated protein, induces chromatin condensation. Mol. Cell. Biol. 26 8303-8315] [Kleivi, K. et al., (2007) Gene expression profiles of primary colorectal carcinomas, liver metastases, and carcinomatoses. Mol. Cancer 6, 1-16].

Based on the establishment of PC4 as an onco-protein, which plays important roles in oncogenesis of different types of human tumors, the present invention provides, in certain embodiments, a method for diagnosing a tumor in a subject, the method comprising providing a suitable tissue sample or liquid sample from the subject, and detecting the level of PC4 protein as a biomarker therein, wherein an elevated PC4 level, as compared to a control sample, indicates that the sample is tumorous. This method may further comprise detecting the level of another related biomarker, such as DNA Topoisomerase I, as additional confirmation.

The present invention further provides a method for detecting the presence of a tumor in a subject, the method comprising providing a suitable sample from the subject, and detecting the level of DNA topoisomerase I protein as a biomarker therein, wherein an elevated DNA topoisomerase I level, as compared to a control sample, indicates that the sample is tumorous.

Furthermore, the present invention provides methods and compositions for treating cancer by decreasing cellular PC4 level or inhibiting its function. In certain embodiments, the present invention provides a method for treating a cancer, comprising administering to a patient in need thereof a pharmaceutical composition comprising an effective amount of a suitable PC4 antagonist. In specific embodiments, the method of treatment is used for treating lung cancer, bladder cancer, colon cancer, breast cancer, endometrial cancer, thyroid cancer, small bowel cancer, ovary cancer, and other malignant tumors.

In certain embodiments, the pharmaceutical composition comprising suitable PC4 antagonist may also be used for prophylactic purposes, to inhibit pathogenesis of human tumors.

In certain embodiments, a suitable treatment method or composition according to the present invention may be based on a modified PC4 peptide. It is known that PC4 is a multi-function protein, as evidenced by its ability to bind to DNA and at the same time interact with other proteins. It is recognized that a modified, non-functional PC4 mutant or a fragment thereof may be negatively dominant over wild type or unmodified PC4 protein in existence in the cell. Alternatively, the modified, non-functional mutant, analog or fragment will compete with the wild type or non-modified protein, thereby effectively lowering the function of the native protein. For example, the PC4 protein or peptide comprising a F77P point mutation or an equivalent thereof, which is known to abolish the DNA binding activity of PC4, can be used for pharmaceutical purposes. A peptidomimetic compound having similar functions would be a highly desired therapeutic agent as it is able to avoid destruction by the animal's immune system or protein metabolism machinery. Also, as phosphorylated PC4 is inactive, it can be used for therapeutic purposes by competing with the unphosphorylated PC4 (active form).

Suitable antagonists of the present invention include antibodies, antisense nucleic acid molecules, and small interfering RNA molecules.

Antibodies

In one embodiment, this invention provides neutralizing antibodies to inhibit the biological action of PC4 protein, or DNA topoisomerase I ("target protein"). An antibody suitable for the present invention may be a polyclonal antibody. Preferably, the antibody is a monoclonal antibody. The antibody may also be isoform-specific. The monoclonal antibody or binding fragment thereof of the invention may be Fab fragments, F(ab)2 fragments, Fab' fragments, F(ab')2 fragments, Fd fragments, Fd' fragments or Fv fragments. Domain antibodies (dAbs) (for review, see Holt et al., 2003, Trends in Biotechnology 21:484-490) are also suitable for the methods of the present invention.

Various methods of producing antibodies with a known antigen are well-known to those ordinarily skilled in the art (see for example, Harlow and Lane, 1988, Antibodies: A Laboratory Manual. Cold Spring Harbor Laboratory Press, Cold Spring Harbor, N.Y.; see also WO 01/25437). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In accordance with the present invention, the antibodies or binding fragments thereof include those which are capable of specific binding to a target protein or an antigenic fragment thereof, preferably an epitope that is recognized by an antibody when the antibody is administered in vivo. Antibodies can be elicited in an animal host by immunization with a target protein-derived immunogenic component, or can be formed by in vitro immunization (sensitization) of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in, e.g., Morrison et al., 1984, Proc. Natl. Acad. Sci. USA, 81:6851-6855; Neuberger et al., 1984, Nature, 312:604-608; and Takeda et al., 1985, Nature, 314:452-454. For human therapeutic purposes, humanized, or more preferably, human antibodies are used.

Further, single chain antibodies are also suitable for the present invention (e.g., U.S. Pat. Nos. 5,476,786 and 5,132,405 to Huston; Huston et al., 1988, Proc. Natl. Acad. Sci. USA, 85:5879-5883; U.S. Pat. No. 4,946,778 to Ladner et al.; Bird, 1988, Science, 242:423-426 and Ward et al., 1989, Nature, 334:544-546). Single chain antibodies are formed by linking the heavy and light immunoglobulin chain fragments of the Fv region via an amino acid bridge, resulting in a single chain polypeptide. Univalent antibodies are also embraced by the present invention.

Many routes of delivery are known to the skilled artisan for delivery of antibodies. For example, direct injection may be suitable for delivering the antibody to the site of interest. It is also, possible to utilize liposomes with antibodies in their membranes to specifically deliver the liposome to the area where target gene expression or function is to be inhibited. These liposomes can be produced such that they contain, in addition to monoclonal antibody, other therapeutic agents, such as those described above, which would then be released at the target site (e.g., Wolff et al., 1984, Biochem. et Biophys. Acta, 802:259).

Antisense Nucleic Acid Molecules

In another embodiment of the invention, antisense oligonucleotides can be used to inhibit the expression of PC4 gene, or a DNA topoisomerase I gene ("target gene"). The expression, preferably constitutively, of antisense RNA in cells has been known to inhibit gene expression, possibly via blockage of translation or inhibition of splicing. In this regard, interference with splicing allows the use of intron sequences which should be less conserved and therefore result in greater specificity, inhibiting expression of a gene product of one species but not its homologue in another species.

The term "antisense component" corresponds to an RNA sequence as well as a DNA sequence, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. This antisense molecule must have sufficient complementarity, about 18-30 nucleotides in length, to the target gene so that the antisense RNA can hybridize to the target gene (or mRNA) and inhibit target gene expression regardless of whether the action is at the level of splicing, transcription, or translation. The antisense components of the present invention may be hybridizable to any of several portions of the target cDNA, including the coding sequence, 3' or 5' untranslated regions, or other intronic sequences, or to target mRNA. One of ordinary skill in the art will readily recognize that the antisense molecules can be easily designed based on the known mRNA sequences.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. In one embodiment, stable transfection and constitutive expression of vectors containing target cDNA fragments in the antisense orientation are achieved, or such expression may be under the control of tissue or development-specific promoters. Delivery can also be achieved by liposomes.

For in vivo therapy, the currently preferred method is direct delivery of antisense oligonucleotides, instead of stable transfection of an antisense cDNA fragment constructed into an expression vector. Antisense oligonucleotides having a size of 15-30 bases in length and with sequences hybridizable to any of several portions of the target cDNA, including the coding sequence, 3' or 5' untranslated regions, or other intronic sequences, or to target mRNA, are preferred. Sequences for the antisense oligonucleotides to target are preferably selected as being the ones that have the most potent antisense effects. Factors that govern a target site for the antisense oligonucleotide sequence include the length of the oligonucleotide, binding affinity, and accessibility of the target sequence. Sequences may be screened in vitro for potency of their antisense activity by measuring inhibition of target protein translation and target related phenotype, e.g., inhibition of cell proliferation in cells in culture. In general it is known that most regions of the RNA (5' and 3' untranslated regions, AUG initiation, coding region, splice junctions and introns) can be targeted using antisense oligonucleotides.

The preferred target antisense oligonucleotides are those oligonucleotides which are stable, have a high resistance to nucleases, possess suitable pharmacokinetics to allow them to traffic to target tissue site at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNase H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

The delivery route will be the one that provides the best antisense effect as measured according to the criteria described above. In vitro and in vivo assays using antisense oligonucleotides have shown that delivery mediated by cationic liposomes, by retroviral vectors and direct delivery are efficient. Another possible delivery mode is targeting using antibody to cell surface markers for the target cells. Antibody to target or to its receptor may serve this purpose.

Small Interfering RNA Molecules

In a further embodiment, the expression of a target gene may be inhibited by small interfering RNAs (siRNA, also known as RNAi, RNA interference nucleic acids). siRNA are double-stranded RNA molecules, typically 21 n.t. in length, that are homologous to the target gene and interfere with the target gene's activity.

siRNA technology relates to a process of sequence-specific post-transcriptional gene repression that can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Indeed the use of relatively short homologous dsRNAs may have certain advantages as discussed below.

Mammalian cells have at least two pathways that are affected by double-stranded RNA (dsRNA). In the siRNA (sequence-specific) pathway, the initiating dsRNA is first broken into short interfering (si) RNAs, as described above. The siRNAs have sense and antisense strands of about 21 nucleotides that form approximately 19 nucleotide siRNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2', 5' oligoadenylate synthetase (2', 5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are preferred to effect gene repression by RNAi (see Hunter et al., 1975, J. Biol. Chem. 250:409-17; Manche et al., 1992, Mol. Cell. Biol. 12:5239-48; Minks et al., 1979, J. Biol. Chem. 254:10180-3; and Elbashir et al., 2001, Nature 411:494-8). siRNA has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass, 2001, Nature 411:428-9). In mammalian cells, siRNAs are effective at concentrations that are several orders of magnitude below the concentrations typically used in antisense experiments (Elbashir et al., 2001, Nature 411:494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al., 2001, Nature 411:494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan.

Exemplary dsRNAs may be synthesized chemically or produced in vitro or in vivo using appropriate expression vectors. Exemplary synthetic RNAs include 21 nucleotide RNAs chemically synthesized using methods known in the art. Synthetic oligonucleotides are preferably deprotected and gel-purified using methods known in the art (see e.g. Elbashir et al., 2001, Genes Dev. 15:188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target nucleic acid.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Although mRNAs are generally thought of as linear molecules containing the information for directing protein synthesis within the sequence of ribonucleotides, most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see, e.g., Jaeger et al, 1989, Proc. Natl. Acad. Sci. USA 86:7706; and Turner et al., 1988, Annu. Rev. Biophys. Biophys. Chem. 17:167). The rules are useful in identification of RNA structural elements and, in particular, for identifying single stranded RNA regions which may represent preferred segments of the mRNA to target for siRNA, ribozyme or antisense technologies. Accordingly, preferred segments of the mRNA target can be identified for design of the siRNA mediating dsRNA oligonucleotides as well as for design of appropriate ribozyme and hammerheadribozyme compositions of the invention (see below).

The dsRNA oligonucleotides may be introduced into the cell by transfection with a heterologous target gene using carrier compositions such as liposomes, which are known in the art—e.g. Lipofectamine 2000 (Life Technologies) as described by the manufacturer for adherent cell lines. Transfection of dsRNA oligonucleotides for targeting endogenous genes may be carried out using Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74). The effectiveness of the siRNA may be assessed by any of a number of assays following introduction of the dsRNAs. These include Western blot analysis using antibodies which recognize the target gene product following sufficient time for turnover of the endogenous pool after new protein synthesis is repressed, reverse transcriptase polymerase chain reaction and Northern blot analysis to determine the level of existing target mRNA.

Further compositions, methods and applications of siRNA technology are provided in U.S. Pat. Nos. 6,278,039, 5,723,750 and 5,244,805, which are incorporated herein by reference.

The present invention in further embodiments provides a method of screening for cancer inhibition agents based on the above discovery that PC4 is an oncoprotein and can be a target for inhibitory compounds. The screening method of the present invention may be, for example, a promoter based screen, using a PC4 promoter sequence (see, e.g., FIG. 1A) linked with a suitable reporter gene such as luciferase or green flurorescence protein gene. A person of ordinary skills in the art will recognize that, aside from the exemplary sequences provided herein, many suitable promoter sequences or other cis-acting transcriptional factors for the PC4 gene are available and may be used.

The screening method of the present invention may also be a protein activity based assay, such as PC4-dependent transcription assays [see, e.g., that which is described in Ge and Roeder (1994) Purification, cloning and characterization of a human coactivator, PC4, that mediates transcriptional activation of class II genes. Cell 78, 513-523], or protein-protein interaction assays, or protein-DNA interaction assays [see, e.g., Ge, H. (2000) UPA, a universal protein array system for quantitative detection of protein-protein, protein-DNA, protein-RNA and protein-ligand interactions. Nucleic Acids Res. 28, e3].

The diagnosis or screening methods of the present invention may be based on many protein or nucleic acid-based assay methods well established and known to those skilled in the art. Anti-PC4 antibody and anti-Topoisomerase I antibodies are known and commercially available. For example, antibodies conjugated with gold nanoparticles can be obtained from BioassayWorks, (Ijamsville, Md.) and can be used for monitoring the level of PC4 protein or Topoisomerase I, rapidly and quantitatively. Similarly RT-PCR (reverse transcriptase-polymerase chain reaction) assay can be used for monitoring the activation of PC4 and DNA topoisomerase I at the RNA level.

One skilled in the art understands that "subject" of the present invention includes human and non-human animals that are susceptible to tumors.

One skilled in the art understands that "cancer therapy" of the present invention includes chemotherapy, radiation therapy, immunotherapy, and combinations thereof.

The cancer inhibition agents of the present invention can be administered to a subject, either alone or in combination with one or more known or unknown cancer inhibition agents, in an effective amount to inhibit or treat cancer. "Effective amount" is understood to be amounts not harmful to the subject where any harmful side effects are outweighed by the benefits. The useful dosage to be administered will vary depending on the age, weight, and subject treated, the mode and route of administration, and the type of cancer or tumor against which inhibition or treatment is sought.

Dosages and routes of administration of the cancer inhibition agents of the present invention can be determined without undue experimentation by one skilled in the art after consideration of all the criteria (including those listed above for specific types of agents) and use of best judgment on the subject's behalf.

Use of mutated PC4 protein as a therapeutic drug to treat PC4-dependent malignant tumors is further contemplated. It has been reported previously that the N-terminal serine-rich domain is essential for PC4 activity and is regulated by casein kinase II phosphorylation. Deletion of the N-terminal region resulted in a complete loss of its coactivator activity. Important amino acids that are required for PC4 activity by generating a series of point mutations are mapped and disclosed herein. Seven mutated PC4 proteins along with the wild type PC4 were expressed, purified, and had their activity tested in 1) electrophoresis mobility shift assay, 2) in vitro transcription assay, and 3) protein array analyses. In addition to a single amino acid change at F77 (F77P) that abolishes PC4's DNA binding activity and transcription activity, two double mutations (K23I/K29A and K35I/K41A) and a triple mutation (R27A/K28I/K29A) at the N-terminal basic region also significantly diminish the PC4 activity. Thus, PC4 mutants F77P, K2I/K29A, K35I/K41A, and R27A/K28I/K29A could be used as cancer inhibition reagents by competing with the endogenous wild type PC4, resulting in a therapeutic effect on PC4-dependent malignant tumors. Zone Name: A1,AMD,M Use of short peptides corresponding to the activation domain of PC4 as cancer inhibition agents is also further contemplated. As a general transcription coactivator, interactions with general transcription factor(s), activator, and template DNA are all required for PC4 activity. Two peptides corresponding to PC4 activation domain amino acid 16-30 (DSDSEVDKKLKRKKQ) (SEQ ID NO: 13) and 26-40 (KRKKQVAPEKPVKKQ) (SEQ ID NO: 11) will be synthesized and their inhibitory effects on PC4 will be tested by competing the interaction of PC4 with the activators in protein-protein interaction and in vitro transcription assays.

Use of an artificial activation domain as a cancer inhibition agent is also contemplated. Because the oncogenic activity of PC4 functions as a transcription coactivator to activate expression of most, if not all, oncogenes, growth factors and other oncogenic factors through interaction with their specific activators, blocking PC4 binding activity with endogenous activators could result in a loss of PC4 activator activity. An amphipathic helix (AH) peptide with 15 amino acids has been tested and could mimic an activation domain interacting strongly with PC4. Fusion with a Gal4 DNA binding domain resulted in dramatic transcription activation in a PC4-dependent manner. The AH peptide (ELQEL'QELQALLQQQ) (SEQ ID NO: 15) will be synthesized and tested for its inhibitory effect on PC4 by competing with other endogenous activators to bind to PC4.

Use of a translocation domain (TLD) to facilitate entry of PC4 protein-related reagents to tumor cells is also contemplated. The translocation domain (TLD) is a short peptide composed of 12 amino acids (PLSSIFSRIGDP) (SEQ ID NO: 17) with a molecular weight of 1288.47 (pI=6.27). It was reported that this peptide is essential for hepatitis B virus infection and cell permeability of other proteins (Oess and Hildt 2000; Stoeckl et al., 2006). In order to allow protein-related cancer inhibition agents to target nuclear onco-protein PC4, TLD will be fused to recombinant monoclonal antibodies, PC4 mutant proteins, peptides corresponding to PC4 activation domains, amphipathic helix peptide, and other proteins or peptides that can inhibit PC4 activity. Other types of translocation domains, such as TLD of HIV tat protein will also be tested.

High throughput system (HTS) for screening compounds that inhibit PC4 activity is also contemplated. The fluorescence resonance energy transfer (FRET) technology has been a useful tool in high throughput screen assays to quantify molecular dynamics such as protein-protein interactions, protein-DNA interactions, and protein conformational changes. A high throughput FRET assay system is developed in a 96-well or 384-well plate format, in which fluorescence labeled Amphipathic helix (AH) domain acts as an energy donor and the fluorescence-labeled PC4 protein acts as an energy acceptor. Once the PC4-AH complex forms where the donor and acceptor are in proximity (1-10 nm) due to the interaction of the two molecules, the PC4 emission is predominantly observed because of the intermolecular FRET from the AH domain to the PC4 protein. The excitation of AH peptide and emission of PC4 can be monitored by a fluorescence plate reader. The inhibitory effect of any compounds can be detected by monitoring the change of reading. These compounds will be further validated and could be developed as potential cancer inhibition drug candidates for PC4-dependent malignant tumors. Two types of compounds will be screened: 1) small synthetic molecules and 2) natural compounds.

Small synthetic molecules include commercially available and in-house collections. After registered incoming compounds are stored in a 96-well or 384-well plate, an inventory database will be established. Each well of a reaction plate contains 1 mM of tested compound in 10-50 ul (10 ul for 384-well plate and 50 ul for 96-well plate) of reaction mixture including fluorescence-labeled PC4 and AH. Each plate contains four wells of positive control (10 mM of unlabeled AH) and four wells of negative control (H2O instead of fluorescence-labeled AH donor). The emission at OD535 is then measured in a plate reader (Molecular Dynamics). Preliminary positive molecules will be further validated using different assays including in vitro protein-protein interaction assay, transcription assay, cell-based assay and animal test before clinical trials.

Natural compounds comprise a major portion of prescription drugs. Over 50% of the anti-tumor and anti-infective agents that are commercially available are of natural product origin. To identify natural molecules that can inhibit PC4 activity, compounds from soil microbes, sea microbes, plants, and other sources will be screened using the HTS PC4-AH FRET assay. Identified crude materials will be further purified, characterized, and validated in different assay systems.

The following examples are provided for illustration purposes only, and are in no way intended to limit the scope of the present invention.

EXAMPLE 1

Materials and Methods

Mutagenesis

Double-stranded oligos that contain specific point mutations were commercially synthesized and used to replace the wild type region of PC4 in a bacterial expression vector to generate different point mutations. Each mutant construct was confirmed by sequencing analysis and expressed in E coli. Bacterially expressing PC4 proteins (including wild type and mutants) were produced by a two-step purification method: 1) P11 phosphocellulose and 2) Heparin sepharose. Concentrations of purified proteins were measured using the Bradford method and the purity was examined using SDS-PAGE.

Electrophoresis Mobility Shift Assay (EMSA)

EMSA was used to determine the ds-DNA binding activity of PC4 protein and was performed in a 20 ul of reaction containing long of purified PC4 protein and $^{32}$P-labeled 64 bp dsDNA probe from the adeno major late promoter region. After incubated at 4° C. for 1 hr, the reaction mixture was analyzed on an 8% polyacrylamide gel. The mobilized PC4-dsDNA complex was visualized using autoradiography.

In Vitro Transcription Assay

In vitro transcription assay was reconstituted with purified general transcription factors, including TFIIA, TFIIB, TFIID, TFIIF, TFIIH and RNA polymerase II, either purified from HeLa cells or from a recombinant source. This system can be activated in a PC4 and activator-dependent manner. In addition to the transcription factors, the system also contained one activator-responsive template, a basic template (activator-independent), and $^{32}$P-CTP. After incubation at 30° C. for 1 hr, the newly synthesized RNAs were extracted and analyzed on a denatured polyacrylamide gel and visualized by autoradiography.

Protein Array Assay

The protein array assay is based on the "Universal Protein Array" method, also called UPA [Ge, H. (2000) UPA, a universal protein array system for quantitative detection of protein-protein, protein-DNA, protein-RNA and protein-ligand interactions. Nucleic Acids Res. 28, e3]. Purified proteins were validated, normalized and arrayed on a nitrocellulose sheet. Each spot was arrayed in 1 mm diameter containing 10-100 ng of protein depending on size. Targeted proteins that interacted with the PC4 proteins on the array were detected by specific antibodies such as antibodies against transcription factor TFIIA, Gal4, or Sp1. For protein-DNA interaction, probe DNA was labeled with $^{32}$P-dCTP and the bound DNA was monitored by autoradiography.

Examination of PC4 Expression During *Xenopus laevis* Metamorphosis

Total protein extracts were prepared from different stages of tadpoles and analyzed using SDS-PAGE. After proteins were transferred to a nitrocellulose membrane, differentially expressed PC4 was detected by Western blot using polyclonal antibodies against human PC4 and visualized by the ECL method.

Confocal Microscopy of PC4-Transfected HeLa Cells

Wild type (WT) or serine-rich region mutations (ΔS) of human PC4 was subcloned into a mammalian expression vector pcDNA3.1 and transfected into HeLa S cells. Two days after transfection, specimens were viewed under a confocal microscope.

Northern Blot Analysis

Total poly A RNAs were isolated from different cell lines and separated on a 1% agarose-formaldehyde gel. After transfer to a nitrocellulose membrane, PC4 mRNA was detected by incubating the membrane with $^{32}$P-labeled PC4 cDNA. 28S and 18S ribosomal RNAs were visualized by EtBr staining.

Examination of PC4 Expression in Tumor Tissues

Different human tumor tissues and paired normal tissues were obtained from the Center of Human Tissue Network of the National Institutes of Health. Total proteins were extracted from different tissues. Expression levels of PC4 and DNA topoisomerase I were detected by Western blot, in which 50 ug of total protein from each tissue was analyzed and incubated with anti-PC4 or anti-Topo I polyclonal antibodies, respectively. For immunohistochemistry (IHC)

analysis, slides that contained normal human lung tissue or lung carcinoma tissue were obtained from the National Institutes of Health. Tissue slides were first treated with xylene for 2×15 min, then they were incubated in decreasing concentrations of ethanol from 100% to 70% for 5 min each interval. After treatment at 95° C. for 5 min, rinse with $H_2O$ and 1×PBS, and blocking with blocking buffer containing 3% dry milk, the slides were incubated with the anti-PC4 polyclonal antibody (1:1000 in blocking buffer) for 1 hr at room temperature. After washing off the excess primary antibody, slides were incubated with the fluorescence-labeled secondary antibody for 30 min. After rinsing the slides, the PC4 antigen was detected under a fluorescence microscope.

EXAMPLE 2

Effects of PC4 Mutations on DNA Binding and Transcription

The N-terminal serine-rich domain of PC4 is known to be essential for PC4 activity and is regulated by casein kinase II phosphorylation. In fact, it is known that deletion of the N-terminal region results in a complete loss of PC4 coactivator activity. The inventor has mapped important amino acids that are required for PC4 activity by generating a series of point mutations (FIG. 2). Accordingly, FIG. 2 shows wild type PC4 (PC4-wt) and five mutations of PC4. The amino acid substitutions at particular residue locations are shown in parentheses below the mutation (i.e., mt) number. Regarding mt5, it is generally known that the amino acid phenylalanine is involved in molecular interactions including protein-protein or protein-DNA interactions. Prior data indicated that the ssDNA binding region of PC4 is located near amino acid residue 77. Seven mutated PC4 proteins along with the wild type PC4 were expressed and purified (FIG. 3A), and examined for activity in 1) electrophoresis mobility shift assay (EMSA, FIG. 3B), 2) in vitro transcription assay (FIG. 3C), and 3) protein array analyses (FIG. 4). In addition to a single amino acid change at F77 (F77P) that abolishes PC4's DNA binding activity and transcription activity, two double mutations (K23I/K29A and K35I/K41A) and a triple mutation (R27A/K28I/K29A) at the N-terminal basic region also significantly diminish the PC4 activity. Thus, PC4 mutants F77P, K2I/K29A, K35I/K41A, and R27A/K28I/K29A could be used as cancer inhibition reagents by competing with the endogenous wild type PC4, resulting in a therapeutic effect on PC4-dependent malignant tumors.

EXAMPLE 3

Effects of PC4 Mutations on Binding of PC4 to DNA and Other Transcription Factors FIG. 4 shows that the amino acid phenylalanine at position 77 is critical for the ssDNA binding activity of PC4 (see mt5 in FIG. 4F). On the other hand, this F77P point mutation (i.e., mt5), enhances the interaction of PC4 with the transcription factors TFIIA (see FIG. 4C) and Sp1 (see FIG. 4E). Other mutations had minimal or no effect on the ability of PC4 to interact with DNA and the proteins Sp1 and TFIIA. Approximately equal presence of wild type PC4 (wt) and individual mutations (mt) was confirmed by Ponceau S staining (FIG. 4A) and detection with anti-PC4 antibody (FIG. 4B). Gal4-(1-94) served as a negative control for PC4 interaction with Gal4-Sp1 fusion protein (FIG. 4E).

EXAMPLE 4

Role of PC4 in Differentiation

Figure 5:
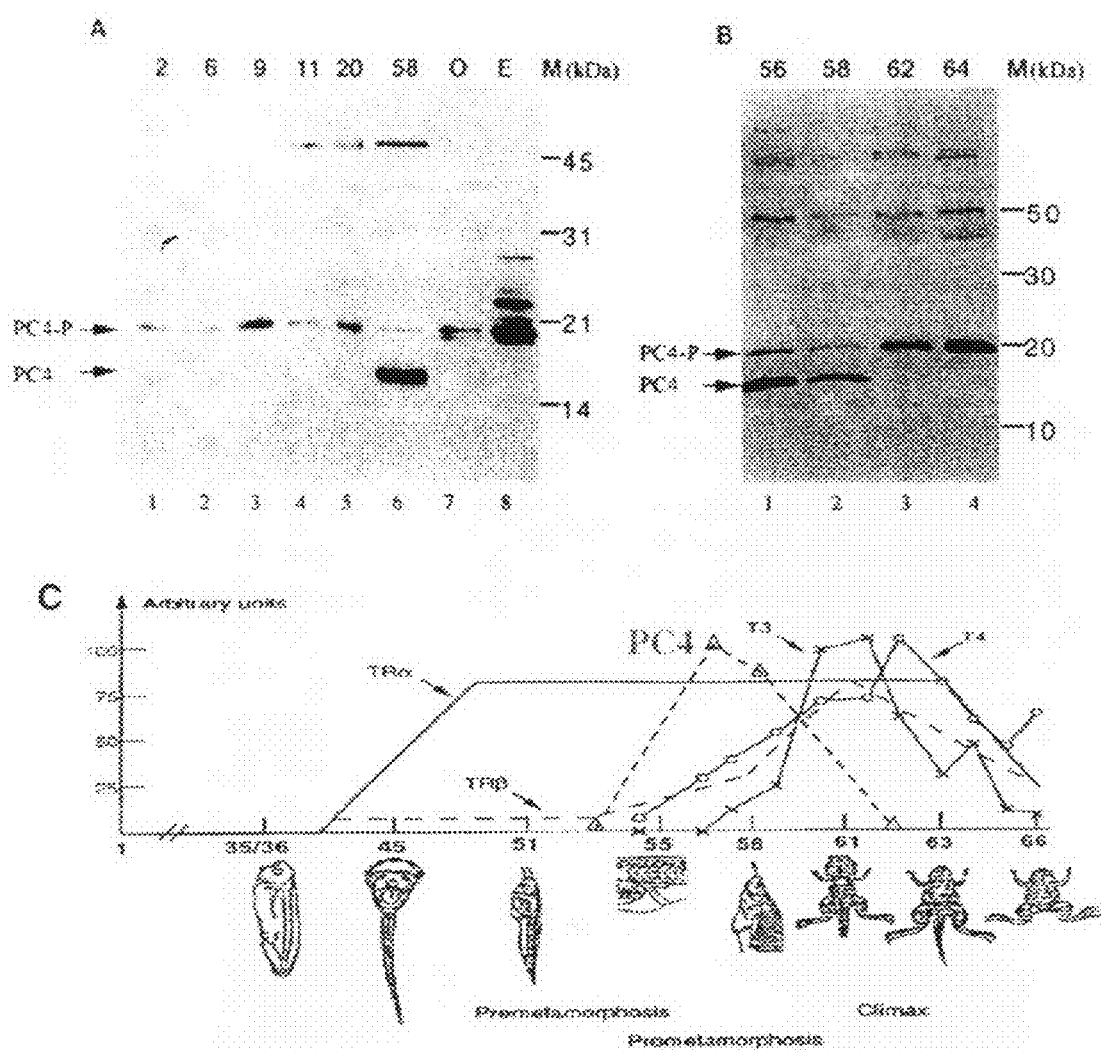
FIGS. 5A, 5B, and 5C illustrate the correlation of PC4 activation with *Xenopus laevis* metamorphosis, in which PC4 is significantly activated between stages 56-58. Individual lanes of the gel represent various stages of tadpole development.

FIGS. 5A, 5B, and 5C show that PC4 activation is required for *Xenopus laevis* metamorphosis. The results show that PC4 is activated between stages 56-58 of tadpole development, as evidenced by the decreased expression of phosphorylated PC4 (i.e., PC4-P) (inactive form of PC4) and increased expression of non-phosphorylated PC4 (active form of PC4). Because metamorphosis requires activation of many growth factors, transcription factors, and nuclear hormone receptors involved in the differentiation process, analogous to the process of metastasis, these data support the link between PC4 and cancer. Metamorphosis of *Xenopus laevis* undergoes a single change from tadpole to an adult (see FIG. 5C). In addition to the requirement of many hormones (such as thyroid hormones T3 and T4), many growth factors, nuclear hormone receptors, and transcription factors (such as thyroid hormone receptors TRα and TRβ) are required for cell growth and differentiation. PC4 may play essential role to activate those factors.

EXAMPLE 5

PC4 Causes Chromosome Condensation in Hela Cells

Figure 6:
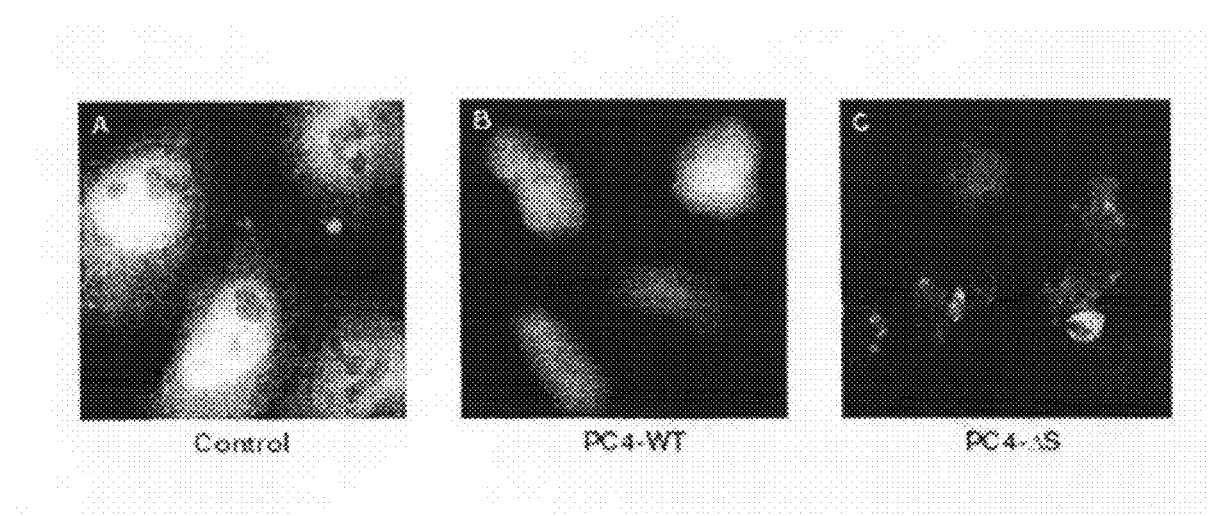
FIGS. 6A, 6B, and 6C show that PC4 is located in the nucleus and causes chromosome condensation and apoptosis when transfected into HeLa cells.

FIG. 6 shows that PC4 is located in the nucleus and causes chromosome condensation and apoptosis when transfected into HeLa cells. Transfection of the cells with wild type PC4 shows that the chromosomes of HeLa cells are condensed (compare FIG. 6A, control, with FIG. 6B, PC4). Transfection with serine-rich region mutation of PC4 (FIG. 6C), which can no longer be phosphorylated by casein kinase II, shows that, in addition to chromosome condensation, the shape of the nucleus and cells are changed (representing a common characteristic of malignant tumor cells). The data support the theory that cancer can be caused by mutation and mutations occur frequently at the centromere region. These data show that PC4 not only binds to the chromosome, it actually binds to centromere, thereby suggesting a potential mechanism of PC4 (i.e., that PC4 functions as an oncogene by preventing other DNA repair enzymes to bind the DNA).

EXAMPLE 6

Expression of PC4 mRNA in Transformed and Tumor Cell Lines

FIG. 7 shows that PC4 mRNA is detectable in all transformed cell lines and breast cancer cell lines, but not in primary NIH3T3 cell line and non-malignant mouse tissues. FIG. 7A represents approximately equal loading of the lanes of the Northern blot with cell line mRNA (as demonstrated by staining for 18S and 28S rRNA). FIG. 7B shows the results of a negative control (human p52 mRNA). FIG. 7C shows hybridization with PC4 cDNA and thus expression of PC4 mRNA in different cell lines.

EXAMPLE 7

Elevated Expression of PC4 Protein in Tumor Tissues

Figure 8:
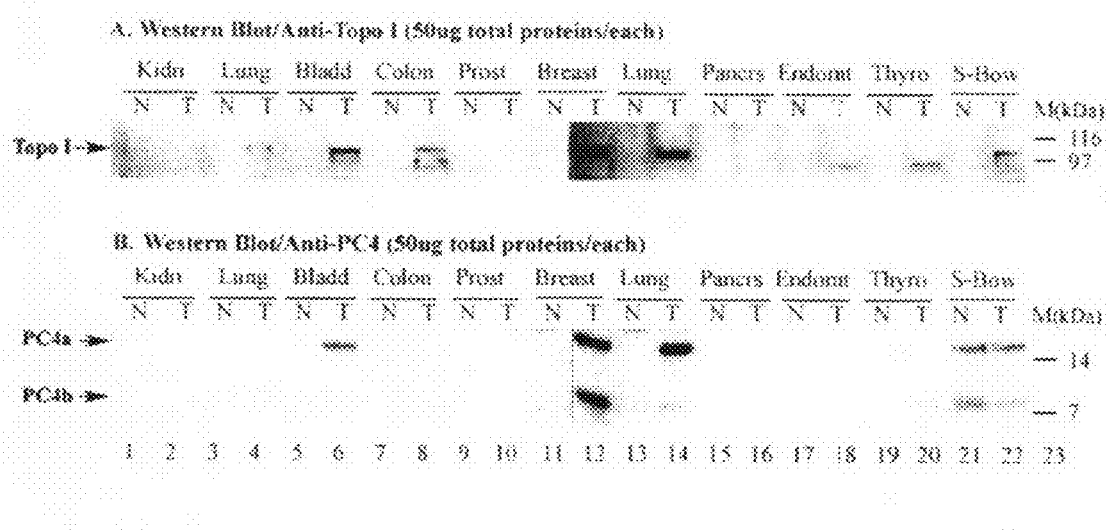
FIGS. 8A and 8B illustrate the results of Western blot analysis of PC4 and topoisomerase I.
Figure 10:
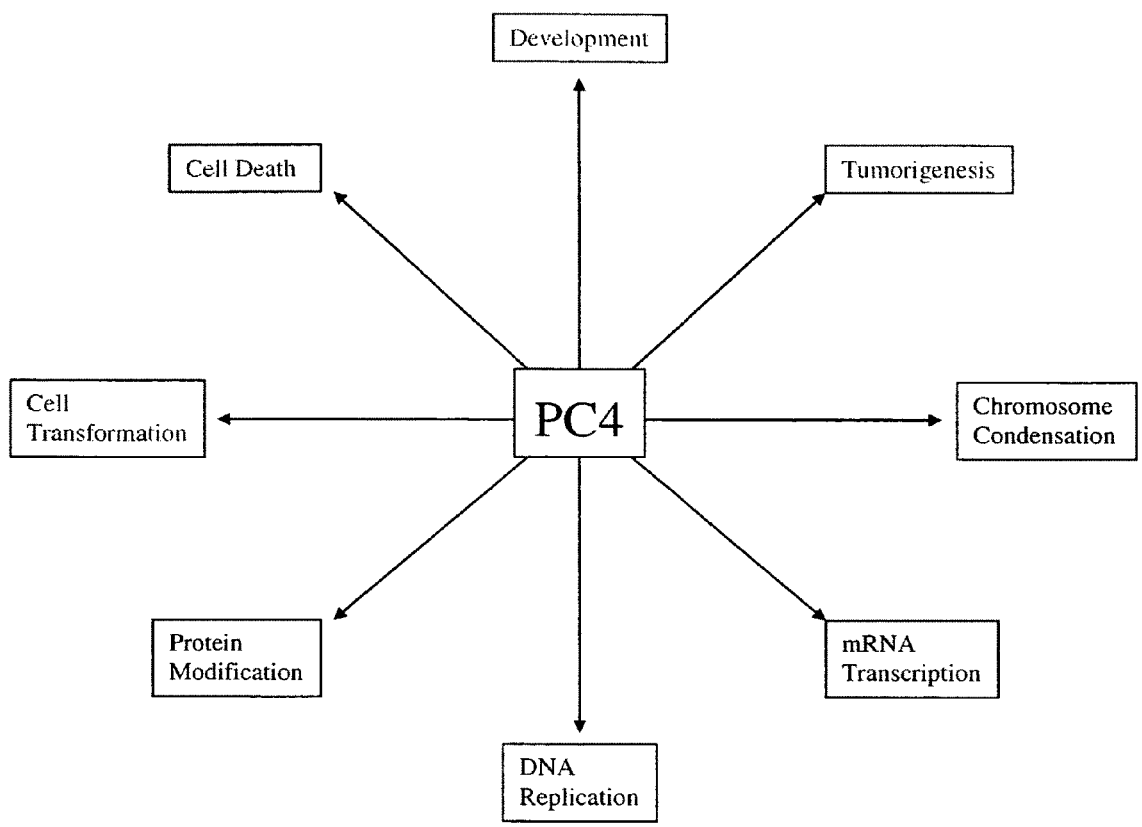
FIG. 10 illustrates the multiple functions of PC4. All these functions relate to or underlie the pathogenesis of cancer and, thus, are likely targets of cancer inhibition agents.

FIG. 8 shows that PC4 protein is detectable by Western blot analysis in a number of human tumor tissues (T), but not in corresponding normal (N) human tissues (FIG. 8B). In addition, the activation of PC4 correlates with the activation of the DNA topoisomerase I (see FIG. 8A), a well-studied target for several cancer inhibition drugs.

EXAMPLE 8

Expression of PC4 Protein in Lung Tumor

FIG. 9 shows that PC4 protein accumulates in all tumor cells of human lung carcinoma tissue (FIG. 9B) but not in normal cells of non-malignant lung tissue (FIG. 9A).

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of classifying a candidate compound as a potential anti-cancer agent comprising: providing a mixture containing PC4 bound to dsDNA; contacting said mixture with a candidate compound; and classifying a candidate compound that shows binding to PC4 as a potential anti-cancer agent.

2. The method of claim 1, wherein the PC4 contains one or more PC4 activation domains, an N-terminal region of PC4, a region of PC4 containing basic amino acids, a PC4 amino acid F77, or combinations thereof.

3. The method of claim 2, wherein the dsDNA binds to the one or more PC4 activation domains, the N-terminal region of PC4, the region of PC4 containing basic amino acids, or the PC4 amino acid F77.

4. The method of claim 3, wherein the one or more PC4 activation domains contain a PC4 domain that contains amino acids 16-30 or amino acids 26-40.

5. The method of claim 1, wherein the dsDNA encodes the sequence of a transcription activation site or a promoter sequence.

6. The method of claim 1, wherein the candidate compound is a candidate anti-tumor compound.

7. The method of claim 1, wherein the potential anti-cancer agent is potentially effective in treatment against cancer of the lung, bladder, colon, breast, endometrium, thyroid, small bowel, ovary, or a combination thereof.

8. The method of claim 1, wherein the potential anti-cancer agent is potentially effective in treatment against cancer cells that show an increased level of topoisomerae 1 activity as compared to a control level.

9. A method of classifying a candidate compound as a potential anti-cancer agent comprising: providing a mixture containing PC4 comprising a PC4 domain that contains amino acids 16-30 (SEQ ID NO:13) or amino acids 26-40 (SEQ ID NO:11) bound to dsDNA; contacting said mixture with a candidate compound; and classifying a candidate compound that decreases binding of PC4 to dsDNA as a potential anti-cancer agent.

10. The method of claim 9, wherein the potential anti-cancer agent is potentially effective in treatment against cancer cells that show an increased level of topoisomerase 1 activity as compared to a control level.

\* \* \* \* \*

SEQUENCE LISTING

```
<160> NUMBER OF SEQ ID NOS: 17

<210> SEQ ID NO 1
<211> LENGTH: 3438
<212> TYPE: DNA
<213> ORGANISM: Homo sapiens
<220> FEATURE:
<221> NAME/KEY: 5'UTR
<222> LOCATION: (1)..(45)
<220> FEATURE:
<221> NAME/KEY: CDS
<222> LOCATION: (46)..(429)
<220> FEATURE:
<221> NAME/KEY: 3'UTR
<222> LOCATION: (430)..(3438)

<400> SEQUENCE: 1
gcgaacgacc aagagggtgt tcgactgcta gagccgagcg aagcg atg cct aaa tca       57
                                                  Met Pro Lys Ser
                                                   1 aag gaa ctt gtt tct tca agc tct tct ggc agt gat tct gac agt gag       105
Lys Glu Leu Val Ser Ser Ser Ser Ser Gly Ser Asp Ser Asp Ser Glu
 5                  10                  15                  20 gtt gac aaa aag tta aag agg aaa aag caa gtt gct cca gaa aaa cct       153
Val Asp Lys Lys Leu Lys Arg Lys Lys Gln Val Ala Pro Glu Lys Pro
                 25                  30                  35 gta aag aaa caa aag aca ggt gag act tcg aga gcc ctg tca tct tct       201
Val Lys Lys Gln Lys Thr Gly Glu Thr Ser Arg Ala Leu Ser Ser Ser
             40                  45                  50 aaa cag agc agc agc agc aga gat gat aac atg ttt cag att ggg aaa       249
Lys Gln Ser Ser Ser Ser Arg Asp Asp Asn Met Phe Gln Ile Gly Lys
         55                  60                  65 atg agg tac gtt agt gtt cgc gat ttt aaa ggc aaa gtg cta att gat       297
Met Arg Tyr Val Ser Val Arg Asp Phe Lys Gly Lys Val Leu Ile Asp
     70                  75                  80 att aga gaa tat tgg atg gat cct gaa ggt gaa atg aaa cca gga aga       345
Ile Arg Glu Tyr Trp Met Asp Pro Glu Gly Glu Met Lys Pro Gly Arg
 85                  90                  95                 100 aaa ggt att tct tta aat cca gaa caa tgg agc cag ctg aag gaa cag       393
Lys Gly Ile Ser Leu Asn Pro Glu Gln Trp Ser Gln Leu Lys Glu Gln
                105                 110                 115 att tct gac att gat gat gca gta aga aaa ctg taa aattcgagcc            439
Ile Ser Asp Ile Asp Asp Ala Val Arg Lys Leu
                120                 125 atataaataa aacctgtact gttctagttg ttttaatctg tcttttttaca ttggcttttg    499 ttttctaaat gttctccaag ctattgtatg tttggattgc agaagaattt gtaagatgaa    559 tactttttttt taatgtgcat tattaaaaat attgagtgaa gctaattgtc aactttatta   619
```

```
aggattactt tgtctgccca ccacctagtg taaaataaaa tcaagtaata caatcttaac    679
tgttgtggcc tttttttgatc ataagagttg gtactgttta aggccaaaag taacagtttt   739
tatagatctt ttagtttcaa ctcagctttt acaataaaaa ggatttgtat tgcattgagt    799
ttataaactt ttggtttgtg aacttcatat ttgatctttt ctcttccaat caaatgtcta   859
ggcttgtttg acttccaccc ccaatggttt ttcactcttt ttatttactt cattttcctt   919
taataactta atctcttcat gttcagtttt tacttcactc tttattcttt tctttgatta   979
tggtatgctt atttggaaag tcagtgaaac tgtcaaaatg ttatctcaat aagatactta   1039
tatgagaact acaatcaccg aatctactgt attcaatatt agcagatcta atttgataaa   1099
caacatggct tgtgtgaaaa ctgagcaggt gtttgtttac ccatagtgtt ctgtgtagtt   1159
attgcttagt ctgcagaaaa taatgactta gatgagatgt ctgacttgct ttcacttatt   1219
aaacatgttc accatgggat gatgtctgta acatcagata ttgttcaact agactaggat   1279
ttaataaaaa ttgtgaaagc ttactggcct aacattttat tttataatat tgggtatgaa   1339
ttatatgtag ccagagatgt cattaagctt tactgttata gtaggtaata tggttagttt   1399
gtagggaaaa gagcatatga gcacatgctt gtgtattttg gcctttgccc cagtagaaca   1459
gaccaatggc attctagact tgatgatact aagttttagc agacactagt aagtggtttg   1519
tatttaacca tactgatgaa gcagacagat tgaggcacag atttttagtgg ctttgtggca   1579 ataaataggg catggtgtgc cttaggaaaa gaatgtttat aaagggaatt ataactgaaa   1639
ttaaaggagg cggcagtgaa gaggaaataa ttctcttcta tctaaatgat atacatatga   1699
tattttgaga tttttataac agcagtggaa cacaattcta ggtagagtag aaaaaggaaa   1759 gtttttaaaga catataaaag attcttgttg acaaattatt tttggtagca aatctcaaat   1819
ggttacctgc tattaaggtc tgccatatta gagttttgca ctattttgct accaagtttg   1879
attcatacat ctaaaacatt ttgtagttac ttgtcaagga cttaatttga aaatcatttg   1939
ccaggccaca tagttatcaa ttttttttttc tatcagctat tctgttgtat ttctaaaaca   1999 tttttttagat gacttttttaa agtatatttta gcagtaacct tatgaggttc aaattggtaa   2059
atctcttgta atttagcctt catcgaataa taggtaccag tgtattaaaa atgtgtatttt   2119 tttgcagccc cttgaaccag agtaggttca gagaaactcc caaagtttgt actttagaca   2179
catcaagctt gattggtaac ttccctcctt tttttggggaa catgtttgtg tcctattaac   2239
ttaattggat agattttttaa atatttctta tttttggcac acggaaaggg tagttcgagt   2299
acagaacttt gattttttggt gtagatgcag agggaatgat gggtaaattt cctaggtttta   2359 tgtgaatttta gggggtgtat gcattttgaa acaatctact aacagatggt gctgaaatct   2419
attacctaca tgttttctag ttgttcagca ttatgttaat gaagcctcca tataaggagt   2479
gtttctctgg cacagttggt aagttgactg ctaacttcat ttaaatgtgt tactggatat   2539
gcagtatact gaaattatta atcagtttgt gtataggaaa agagaactgg gttaaaagca   2599
aattaacttg ttctgaaaag aaagtataga ttaattttgt tttctgtttta aattttatct   2659 ccttggtaaa gatttttttttt cctgggcaga aaacttggca ttttttaggcg tagataccttt   2719 accttacaat gccaaaatga atttaattcc agtactcagg ttttttccctt taacagactc   2779 tatgtgtatc agggctttct aatgggtttt tcctcttcgt tttaaaatg tgagtagcat   2839 ttgaccaatt tccagtgctc ttagcatttt acttaaagaa caaccactac aaaagaaaat   2899
ctttgtaatt tgattgtctt ttgctttgct tcattaatgc ctaagaactt aagaatactc   2959
ctacctcatt agctactcaa gatgctgtga cgatcaaatc tattctacat aatgcgttta   3019
```

```
gaaacaaaga cttgggtgaa aaatgaaata agtatattct gacttggcta ttgaggggaa    3079
aattcagtat taagtgttcc tcacaggaga tatgttagca gaatactata aaagtttgaa    3139
atttttaaaa agtaaaagta cttaaattta ggtatctctc ctgaaattct ttgcagttca    3199 tttttatgg cagttaatcc agtgaaacac tcaaaagttt tttttttttt taaaagtgtt     3259
tttccagata aactgtaggg tgaacattca cataatcaca aatatgtaat tctgtaattg    3319
tggaatgctt gtatgctttg ttttcgtaca tcttccatgg agatgtctga atataatact    3379
ccatctgtga atattttaaa tgttgaaata aaagtaagaa atgtgaaaaa aaaaaaaaa     3438
```

<210> SEQ ID NO 2
<211> LENGTH: 127
<212> TYPE: PRT
<213> ORGANISM: Homo sapiens

<400> SEQUENCE: 2

```
Met Pro Lys Ser Lys Glu Leu Val Ser Ser Ser Ser Gly Ser Asp
1               5                   10                  15

Ser Asp Ser Glu Val Asp Lys Lys Leu Lys Arg Lys Lys Gln Val Ala
                20                  25                  30

Pro Glu Lys Pro Val Lys Lys Gln Lys Thr Gly Glu Thr Ser Arg Ala
            35                  40                  45

Leu Ser Ser Ser Lys Gln Ser Ser Ser Arg Asp Asp Asn Met Phe
        50                  55                  60

Gln Ile Gly Lys Met Arg Tyr Val Ser Val Arg Asp Phe Lys Gly Lys
65                  70                  75                  80

Val Leu Ile Asp Ile Arg Glu Tyr Trp Met Asp Pro Glu Gly Glu Met
                85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
        115                 120                 125
```

<210> SEQ ID NO 3
<211> LENGTH: 384
<212> TYPE: DNA
<213> ORGANISM: Homo sapiens

<400> SEQUENCE: 3

```
atgcctaaat caaaggaact tgtttcttca agctcttctg gcagtgattc tgacagtgag    60
gttgacaaaa agttaaagag gaaaaagcaa gttgctccag aaaaacctgt aaagaaacaa   120
aagacaggtg agacttcgag agccctgtca tcttctaaac agagcagcag cagcagagat   180
gataacatgt ttcagattgg gaaaatgagg tacgttagtg ttcgcgattt taaaggcaaa   240
gtgctaattg atattagaga atattggatg gatcctgaag gtgaaatgaa accaggaaga   300
aaaggtattt ctttaaatcc agaacaatgg agccagctga aggaacagat ttctgacatt   360
gatgatgcag taagaaaact gtaa                                          384
```

<210> SEQ ID NO 4
<211> LENGTH: 127
<212> TYPE: PRT
<213> ORGANISM: Artificial Sequence
<220> FEATURE:
<223> OTHER INFORMATION: mt1 (K23I/K29A)

<400> SEQUENCE: 4

Met Pro Lys Ser Lys Glu Leu Val Ser Ser Ser Ser Ser Gly Ser Asp

```
                1               5                  10                 15
Ser Asp Ser Glu Val Asp Ile Lys Leu Lys Arg Lys Ala Gln Val Ala
                    20                  25                  30

Pro Glu Lys Pro Val Lys Lys Gln Lys Thr Gly Glu Thr Ser Arg Ala
                    35                  40                  45

Leu Ser Ser Ser Lys Gln Ser Ser Ser Ser Arg Asp Asp Asn Met Phe
                    50                  55                  60

Gln Ile Gly Lys Met Arg Tyr Val Ser Val Arg Asp Phe Lys Gly Lys
 65                      70                  75                  80

Val Leu Ile Asp Ile Arg Glu Tyr Trp Met Asp Pro Glu Gly Glu Met
                         85                  90                  95

Lys Pro Gly Arg Lys Gly Ile Ser Leu Asn Pro Glu Gln Trp Ser Gln
                    100                 105                 110

Leu Lys Glu Gln Ile Ser Asp Ile Asp Asp Ala Val Arg Lys Leu
                    115                 120                 125
```

<210> SEQ ID NO 5
<211> LENGTH: 127
<212> TYPE: PRT
<213> ORGANISM: Artificial Sequence
<220> FEATURE:
<223> OTHER INFORMATION: mt2 (K35I/K41A)

<400> SEQUENCE: 5

```
Met Pro Lys Ser Lys Glu Leu Val Ser Ser Ser Ser Gly Ser Asp
 1               5                  10                  15

Ser Asp Ser Glu Val Asp Lys Lys Leu Lys Arg Lys Lys Gln Val Ala
                    20                  25                  30

Pro Glu Ile Pro Val Lys Lys Gln Ala Thr Gly Glu Thr Ser Arg Ala
                    35                  40                  45

Leu Ser Ser Ser Lys Gln Ser Ser Ser Ser Arg Asp Asp Asn Met Phe
                    50                  55                  60

Gln Ile Gly Lys Met Arg Tyr Val Ser Val Arg Asp Phe Lys Gly Lys
 65                      70                  75                  80

Val Leu Ile Asp Ile Arg Glu Tyr Trp Met Asp Pro Glu Gly Glu Met
                         85                  90                  95

Lys Pro Gly Arg Lys Gly Ile Ser Leu Asn Pro Glu Gln Trp Ser Gln
                    100                 105                 110

Leu Lys Glu Gln Ile Ser Asp Ile Asp Asp Ala Val Arg Lys Leu
                    115                 120                 125
```

<210> SEQ ID NO 6
<211> LENGTH: 127
<212> TYPE: PRT
<213> ORGANISM: Artificial Sequence
<220> FEATURE:
<223> OTHER INFORMATION: mt3 (R27A/K28I/K29A)

<400> SEQUENCE: 6

```
Met Pro Lys Ser Lys Glu Leu Val Ser Ser Ser Ser Gly Ser Asp
 1               5                  10                  15

Ser Asp Ser Glu Val Asp Lys Lys Leu Lys Ala Ile Ala Gln Val Ala
                    20                  25                  30

Pro Glu Lys Pro Val Lys Lys Gln Lys Thr Gly Glu Thr Ser Arg Ala
                    35                  40                  45

Leu Ser Ser Ser Lys Gln Ser Ser Ser Ser Arg Asp Asp Asn Met Phe
                    50                  55                  60

Gln Ile Gly Lys Met Arg Tyr Val Ser Val Arg Asp Phe Lys Gly Lys
```

```
                        65                  70                  75                  80
Val Leu Ile Asp Ile Arg Glu Tyr Trp Met Asp Pro Glu Gly Glu Met
                        85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
            115                 120                 125

<210> SEQ ID NO 7
<211> LENGTH: 127
<212> TYPE: PRT
<213> ORGANISM: Artificial Sequence
<220> FEATURE:
<223> OTHER INFORMATION: mt4 (R47N/K53I/R59A)

<400> SEQUENCE: 7

Met Pro Lys Ser Lys Glu Leu Val Ser Ser Ser Ser Gly Ser Asp
1               5                   10                  15

Ser Asp Ser Glu Val Asp Lys Lys Leu Lys Arg Lys Gln Val Ala
            20                  25                  30

Pro Glu Lys Pro Val Lys Gln Lys Thr Gly Glu Thr Ser Asn Ala
            35                  40                  45

Leu Ser Ser Ile Gln Ser Ser Ser Ala Asp Asp Asn Met Phe
    50                  55                  60

Gln Ile Gly Lys Met Arg Tyr Val Ser Val Arg Asp Phe Lys Gly Lys
65                  70                  75                  80

Val Leu Ile Asp Ile Arg Glu Tyr Trp Met Asp Pro Glu Gly Glu Met
                        85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
            115                 120                 125

<210> SEQ ID NO 8
<211> LENGTH: 127
<212> TYPE: PRT
<213> ORGANISM: Artificial Sequence
<220> FEATURE:
<223> OTHER INFORMATION: mt6 (K29A)

<400> SEQUENCE: 8

Met Pro Lys Ser Lys Glu Leu Val Ser Ser Ser Ser Gly Ser Asp
1               5                   10                  15

Ser Asp Ser Glu Val Asp Lys Lys Leu Lys Arg Lys Ala Gln Val Ala
            20                  25                  30

Pro Glu Lys Pro Val Lys Gln Lys Thr Gly Glu Thr Ser Arg Ala
            35                  40                  45

Leu Ser Ser Lys Gln Ser Ser Ser Arg Asp Asp Asn Met Phe
    50                  55                  60

Gln Ile Gly Lys Met Arg Tyr Val Ser Val Arg Asp Phe Lys Gly Lys
65                  70                  75                  80

Val Leu Ile Asp Ile Arg Glu Tyr Trp Met Asp Pro Glu Gly Glu Met
                        85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
            115                 120                 125
```

```
<210> SEQ ID NO 9
<211> LENGTH: 127
<212> TYPE: PRT
<213> ORGANISM: Artificial Sequence
<220> FEATURE:
<223> OTHER INFORMATION: mt7 (K41A)

<400> SEQUENCE: 9

Met Pro Lys Ser Lys Glu Leu Val Ser Ser Ser Ser Gly Ser Asp
1               5                   10                  15

Ser Asp Ser Glu Val Asp Lys Lys Leu Lys Arg Lys Lys Gln Val Ala
            20                  25                  30

Pro Glu Lys Pro Val Lys Lys Gln Ala Thr Gly Glu Thr Ser Arg Ala
        35                  40                  45

Leu Ser Ser Ser Lys Gln Ser Ser Ser Arg Asp Asp Asn Met Phe
50                      55                  60

Gln Ile Gly Lys Met Arg Tyr Val Ser Val Arg Asp Phe Lys Gly Lys
65                  70                  75                  80

Val Leu Ile Asp Ile Arg Glu Tyr Trp Met Asp Pro Glu Gly Glu Met
                85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
        115                 120                 125

<210> SEQ ID NO 10
<211> LENGTH: 127
<212> TYPE: PRT
<213> ORGANISM: Artificial Sequence
<220> FEATURE:
<223> OTHER INFORMATION: mt5 (F77P)

<400> SEQUENCE: 10

Met Pro Lys Ser Lys Glu Leu Val Ser Ser Ser Ser Gly Ser Asp
1               5                   10                  15

Ser Asp Ser Glu Val Asp Lys Lys Leu Lys Arg Lys Lys Gln Val Ala
            20                  25                  30

Pro Glu Lys Pro Val Lys Lys Gln Lys Thr Gly Glu Thr Ser Arg Ala
        35                  40                  45

Leu Ser Ser Ser Lys Gln Ser Ser Ser Arg Asp Asp Asn Met Phe
50                      55                  60

Gln Ile Gly Lys Met Arg Tyr Val Ser Val Arg Asp Pro Lys Gly Lys
65                  70                  75                  80

Val Leu Ile Asp Ile Arg Glu Tyr Trp Met Asp Pro Glu Gly Glu Met
                85                  90                  95

Lys Pro Gly Arg Lys Gly Ile Ser Leu Asn Pro Glu Gln Trp Ser Gln
            100                 105                 110

Leu Lys Glu Gln Ile Ser Asp Ile Asp Asp Ala Val Arg Lys Leu
        115                 120                 125

<210> SEQ ID NO 11
<211> LENGTH: 15
<212> TYPE: PRT
<213> ORGANISM: Artificial Sequence
<220> FEATURE:
<223> OTHER INFORMATION: PC4-AD15

<400> SEQUENCE: 11

Lys Arg Lys Lys Gln Val Ala Pro Glu Lys Pro Val Lys Lys Gln
1               5                   10                  15
```

```
<210> SEQ ID NO 12
<211> LENGTH: 27
<212> TYPE: PRT
<213> ORGANISM: Artificial Sequence
<220> FEATURE:
<223> OTHER INFORMATION: TLD-AD15

<400> SEQUENCE: 12

Pro Leu Ser Ser Ile Phe Ser Arg Ile Gly Asp Pro Lys Arg Lys Lys
1               5                   10                  15

Gln Val Ala Pro Glu Lys Pro Val Lys Lys Gln
            20                  25

<210> SEQ ID NO 13
<211> LENGTH: 15
<212> TYPE: PRT
<213> ORGANISM: Artificial Sequence
<220> FEATURE:
<223> OTHER INFORMATION: PC4-S15

<400> SEQUENCE: 13

Asp Ser Asp Ser Glu Val Asp Lys Lys Leu Lys Arg Lys Lys Gln
1               5                   10                  15

<210> SEQ ID NO 14
<211> LENGTH: 27
<212> TYPE: PRT
<213> ORGANISM: Artificial Sequence
<220> FEATURE:
<223> OTHER INFORMATION: TLD-S15

<400> SEQUENCE: 14

Pro Leu Ser Ser Ile Phe Ser Arg Ile Gly Asp Pro Asp Ser Asp Ser
1               5                   10                  15

Glu Val Asp Lys Lys Leu Lys Arg Lys Lys Gln
            20                  25

<210> SEQ ID NO 15
<211> LENGTH: 15
<212> TYPE: PRT
<213> ORGANISM: Artificial Sequence
<220> FEATURE:
<223> OTHER INFORMATION: AH15

<400> SEQUENCE: 15

Glu Leu Gln Glu Leu Gln Glu Leu Gln Ala Leu Leu Gln Gln Gln
1               5                   10                  15

<210> SEQ ID NO 16
<211> LENGTH: 27
<212> TYPE: PRT
<213> ORGANISM: Artificial Sequence
<220> FEATURE:
<223> OTHER INFORMATION: TLD-AH15

<400> SEQUENCE: 16

Pro Leu Ser Ser Ile Phe Ser Arg Ile Gly Asp Pro Glu Leu Gln Glu
1               5                   10                  15

Leu Gln Glu Leu Gln Ala Leu Leu Gln Gln Gln
            20                  25

<210> SEQ ID NO 17
<211> LENGTH: 12
<212> TYPE: PRT
<213> ORGANISM: Artificial Sequence
<220> FEATURE:
```

```
<223> OTHER INFORMATION: TLD12

<400> SEQUENCE: 17

Pro Leu Ser Ser Ile Phe Ser Arg Ile Gly Asp Pro
1               5                   10
```